US011319201B2

(12) United States Patent
Zumbrum et al.

(10) Patent No.: US 11,319,201 B2
(45) Date of Patent: May 3, 2022

(54) SYSTEM FOR SIMULTANEOUS FILLING OF MULTIPLE CONTAINERS

(71) Applicant: Sartorius Stedim North America, Inc., Bohemia, NY (US)

(72) Inventors: Michael A. Zumbrum, New Oxford, PA (US); William Kimmick, Bohemia, NY (US); Kevin Perdue, Bohemia, NY (US); Jan Neuhaus, Bohemia, NY (US)

(73) Assignee: Sartorius Stedim North America Inc., Bohemia, NY (US)

( * ) Notice: Subject to any disclaimer, the term of this patent is extended or adjusted under 35 U.S.C. 154(b) by 89 days.

(21) Appl. No.: 16/519,345

(22) Filed: Jul. 23, 2019

(65) Prior Publication Data

US 2021/0024338 A1    Jan. 28, 2021

(51) Int. Cl.
*B67C 3/22* (2006.01)
*B67C 3/24* (2006.01)
*B67C 3/26* (2006.01)

(52) U.S. Cl.
CPC ............... *B67C 3/225* (2013.01); *B67C 3/24* (2013.01); *B67C 3/26* (2013.01); *B67C 2003/2602* (2013.01)

(58) Field of Classification Search
CPC .. B67C 3/24; B67C 3/26; B67C 3/225; B67C 3/2602; F16K 27/06–067; A61J 1/10;
(Continued)

(56) References Cited

U.S. PATENT DOCUMENTS 553,734 A * 1/1896 Iredale .................... B65B 3/32
141/242
1,438,899 A 12/1922 Cassidy
(Continued)

FOREIGN PATENT DOCUMENTS

CN        102218226      10/2011
DE        3505492 A1     8/1986
(Continued)

OTHER PUBLICATIONS

Basic Science Concepts and Applicants, at p. 312; ISBN 9781583212332, 1583212337 (published 2003) (Year: 2003).*
(Continued)

*Primary Examiner* — Andrew D St. Clair
(74) *Attorney, Agent, or Firm* — Womble Bond Dickinson (US) LLP

(57) ABSTRACT

A fluid distribution system is configured to distribute fluid from a first vessel to second vessels includes a hub assembly and a frame assembly. The hub assembly has an input cap, a distribution cap, a first clamp, and a second clamp. The input cap defines an inlet and the distribution cap is sealingly secured to the input cap with a plenum being defined between the input and distribution caps. The distribution cap includes conduit connectors that each defines an outlet in fluid communication with the plenum. The first clamp is disposed over the distribution cap and is engaged with the input cap to secure the input cap to the distribution cap and the second clamp is disposed over the input cap and engaged with the distribution cap to secure the distribution cap to the input cap. The frame assembly supports the hub assembly and is configured to secure each of the secondary vessels at a predetermined distance relative to the hub assembly.

20 Claims, 7 Drawing Sheets

(58) Field of Classification Search
CPC ......... A61J 1/12; A61J 1/1481; B67D 3/0029; B67D 3/0032; B67D 3/0035
USPC .............. 222/330; 137/561 A; 141/236, 244
See application file for complete search history.

(56) References Cited

U.S. PATENT DOCUMENTS

| | | | |
|---|---|---|---|
| 1,577,539 A | 3/1926 | Hamilton |
| 1,834,085 A | 12/1931 | Bloom |
| 2,186,908 A | 1/1940 | Page et al. |
| 2,191,495 A | 2/1940 | Nesset |
| 2,226,312 A | 12/1940 | Kuhns |
| 2,439,572 A | 4/1948 | Baruch |
| 2,460,542 A | 2/1949 | Smith |
| 2,744,661 A | 5/1956 | Davis |
| 3,130,260 A | 4/1964 | Gray |
| 3,276,447 A | 10/1966 | Hamilton |
| 3,354,012 A | 11/1967 | Forman et al. |
| 3,360,008 A | 12/1967 | Papale et al. |
| 3,458,619 A | 7/1969 | Prochaska |
| 3,467,270 A | 9/1969 | Eady |
| 3,499,568 A | 3/1970 | Riera |
| 3,793,672 A | 2/1974 | Wetmore |
| 3,794,333 A | 2/1974 | Czernik et al. |
| 3,938,035 A | 2/1976 | Fletcher et al. |
| 4,032,311 A | 6/1977 | Bohmrich et al. |
| 4,045,860 A | 9/1977 | Winckler |
| 4,080,989 A | 3/1978 | Chapelsky et al. |
| 4,116,199 A | 9/1978 | Bryne |
| 4,165,814 A | 8/1979 | Seel |
| 4,174,743 A | 11/1979 | Beny et al. |
| 4,334,993 A | 6/1982 | Norton |
| 4,335,717 A | 6/1982 | Bujan et al. |
| 4,336,802 A | 6/1982 | Stone et al. |
| 4,360,776 A | 11/1982 | Bauman |
| 4,396,016 A | 8/1983 | Becker |
| 4,499,148 A | 2/1985 | Goodale et al. |
| 4,581,012 A | 4/1986 | Brown et al. |
| 4,676,898 A | 6/1987 | Saxena |
| 4,700,861 A | 10/1987 | Neward |
| 4,701,159 A | 10/1987 | Brown et al. |
| 4,715,359 A | 12/1987 | Ryo |
| 4,784,299 A | 11/1988 | Stenger |
| 4,785,974 A | 11/1988 | Rudick et al. |
| 4,863,030 A | 9/1989 | Bayer et al. |
| 4,938,371 A | 7/1990 | Vercillo |
| 4,993,573 A | 2/1991 | Freidel et al. |
| 5,025,955 A | 6/1991 | Stenger |
| 5,052,105 A | 10/1991 | Mische et al. |
| D324,568 S | 3/1992 | Marken |
| 5,100,010 A | 3/1992 | Waters |
| 5,114,045 A | 5/1992 | Herpe |
| 5,197,895 A | 3/1993 | Stupecky |
| 5,219,185 A | 6/1993 | Oddenino |
| 5,245,955 A | 9/1993 | Husted |
| 5,250,041 A | 10/1993 | Folden et al. |
| 5,300,060 A | 4/1994 | Nelson |
| 5,350,080 A | 9/1994 | Brown et al. |
| 5,358,872 A | 10/1994 | Mussi et al. |
| 5,362,642 A | 11/1994 | Kern |
| 5,381,839 A * | 1/1995 | Dowd ....................... B65B 3/30 |
| | | | 141/237 |
| H1430 H | 4/1995 | Apel et al. |
| 5,441,197 A | 8/1995 | Gellert et al. |
| 5,476,116 A | 12/1995 | Price et al. |
| 5,478,119 A | 12/1995 | Dye |
| 5,492,531 A | 2/1996 | Post et al. |
| 5,505,495 A | 4/1996 | Godeau |
| 5,507,904 A | 4/1996 | Fisher et al. |
| 5,518,047 A | 5/1996 | Alexandrowski |
| 5,522,155 A | 6/1996 | Bradford |
| 5,695,215 A | 12/1997 | Headley et al. |
| 5,733,452 A | 3/1998 | Whitlock |
| 5,839,471 A * | 11/1998 | Yang ............... G05D 23/1313 |
| | | | 137/625.18 |
| 5,988,422 A | 11/1999 | Vallot |
| 6,032,543 A * | 3/2000 | Årthun ................ C12M 33/04 |
| | | | 73/863.84 |
| 6,039,718 A | 3/2000 | Niedospial, Jr. |
| 6,062,440 A | 5/2000 | Murray et al. |
| 6,071,005 A | 6/2000 | Ekambaram et al. |
| 6,095,356 A | 8/2000 | Rits |
| 6,158,484 A * | 12/2000 | Greenlee ................ A47G 33/02 |
| | | | 141/242 |
| 6,165,362 A | 12/2000 | Nohren et al. |
| 6,179,823 B1 | 1/2001 | Niedospial |
| 6,223,938 B1 | 5/2001 | Pare et al. |
| 6,225,562 B1 | 5/2001 | Fujishita et al. |
| 6,234,545 B1 | 5/2001 | Babuder et al. |
| 6,290,265 B1 | 9/2001 | Warburton-Pitt et al. |
| 6,334,888 B1 | 1/2002 | Collas et al. |
| 6,340,033 B2 | 1/2002 | Paradis et al. |
| 6,354,636 B2 | 3/2002 | Matsuzawa et al. |
| 6,430,033 B1 | 8/2002 | Mitsui et al. |
| 6,499,618 B1 | 12/2002 | Leclerc et al. |
| 6,520,505 B1 | 2/2003 | Koegler et al. |
| 6,523,711 B1 | 2/2003 | Hughes et al. |
| 6,578,802 B1 * | 6/2003 | Thier .................. B67D 3/0009 |
| | | | 248/146 |
| 6,581,637 B2 | 6/2003 | Hamamoto et al. |
| 6,610,200 B1 | 8/2003 | Leijon et al. |
| 6,719,037 B2 | 4/2004 | Crook |
| 6,733,730 B1 | 5/2004 | Griffiths et al. |
| 6,779,575 B1 | 8/2004 | Arthun |
| 6,905,595 B2 | 6/2005 | Gebauer |
| 6,966,581 B2 | 11/2005 | Mastropaolo |
| 6,994,699 B2 | 2/2006 | Houwaert et al. |
| 7,087,047 B2 | 8/2006 | Kraus et al. |
| 7,093,859 B2 | 8/2006 | Warburton-Pitt et al. |
| 7,140,404 B2 | 11/2006 | Cupples et al. |
| 7,293,477 B2 | 11/2007 | Furey et al. |
| 7,306,583 B2 | 12/2007 | Goudaliez et al. |
| 7,407,612 B2 | 8/2008 | Warburton-Pitt et al. |
| 7,497,130 B2 | 3/2009 | Woods et al. |
| 7,500,949 B2 | 3/2009 | Gottlieb et al. |
| 7,563,243 B2 | 7/2009 | Mendels |
| 7,686,037 B2 | 3/2010 | Krywitsky |
| 7,708,923 B1 | 5/2010 | Helicke et al. |
| 7,731,241 B2 | 6/2010 | Aoki et al. |
| 7,784,630 B2 | 8/2010 | Walsh |
| 7,874,467 B2 | 1/2011 | Pardes et al. |
| 7,931,859 B2 | 4/2011 | Mlodzinski et al. |
| 8,008,065 B2 | 8/2011 | Selker et al. |
| 8,025,271 B2 | 9/2011 | Kolodner et al. |
| 8,092,409 B2 | 1/2012 | Miros et al. |
| 8,196,614 B2 | 6/2012 | Kriheli |
| 8,235,067 B2 | 8/2012 | Gagne et al. |
| 8,281,807 B2 | 10/2012 | Trombley et al. |
| 8,336,313 B2 | 12/2012 | McMasters et al. |
| 8,342,737 B2 | 1/2013 | Greller et al. |
| 8,372,058 B2 | 2/2013 | Schilp et al. |
| 8,505,396 B2 | 8/2013 | Zumbrum |
| 8,505,586 B2 | 8/2013 | Zumbrum |
| 8,524,174 B2 | 9/2013 | Yobas et al. |
| 8,562,572 B2 | 10/2013 | Proulx et al. |
| 8,573,424 B2 | 11/2013 | Dubs et al. |
| 8,690,120 B2 | 4/2014 | Hartnett et al. |
| 8,865,427 B2 | 10/2014 | Poo et al. |
| 8,871,317 B2 | 10/2014 | Cai et al. |
| 9,095,693 B2 | 8/2015 | Buisson |
| 9,211,364 B2 | 12/2015 | Croizat et al. |
| 9,227,046 B1 | 1/2016 | Douglas |
| 9,259,563 B2 | 2/2016 | Klingel et al. |
| 9,358,333 B2 | 6/2016 | Trombley, III et al. |
| 9,376,224 B2 | 6/2016 | Gonnelli et al. |
| 9,376,305 B2 | 6/2016 | Zumbrum |
| 9,526,886 B2 | 12/2016 | Mastri et al. |
| 9,528,632 B2 | 12/2016 | Glaun |
| 9,550,969 B2 | 1/2017 | Chotteau et al. |
| 9,597,732 B2 | 3/2017 | Lewis et al. |
| 9,675,520 B2 | 6/2017 | Rogers et al. |
| 9,700,844 B2 | 7/2017 | Schick |
| 9,706,793 B2 | 7/2017 | Hayakawa |
| 9,726,314 B2 | 8/2017 | Py |

(56) References Cited

U.S. PATENT DOCUMENTS

| | | |
|---|---|---|
| 9,771,629 B2 | 9/2017 | Soloway |
| 9,784,111 B2 | 10/2017 | Luo et al. |
| 9,802,172 B2 | 10/2017 | Danders et al. |
| 9,857,002 B2 | 1/2018 | Ott et al. |
| 9,901,729 B2 | 2/2018 | Vigna et al. |
| 9,907,728 B2 | 3/2018 | Kyle et al. |
| 9,926,185 B2 | 3/2018 | Davis et al. |
| 9,938,128 B2 | 4/2018 | Py et al. |
| 9,944,510 B2 | 4/2018 | Zumbrum |
| 9,975,753 B1 | 5/2018 | Zumbrum et al. |
| 9,987,508 B2 | 6/2018 | Cockerham et al. |
| 10,006,567 B2 | 6/2018 | Zumbrum |
| 10,486,959 B2 | 11/2019 | Zumbrum |
| 2001/0015226 A1 | 8/2001 | Hamamoto et al. |
| 2001/0017161 A1 | 8/2001 | Paradis et al. |
| 2001/0035093 A1 | 11/2001 | Yokota |
| 2002/0162648 A1 | 11/2002 | Crook |
| 2002/0185186 A1 | 12/2002 | Juliar et al. |
| 2003/0052074 A1 | 3/2003 | Chang et al. |
| 2003/0208151 A1 | 11/2003 | Kraus et al. |
| 2004/0026265 A1 | 2/2004 | Nadanami et al. |
| 2004/0064086 A1 | 4/2004 | Gottlieb et al. |
| 2004/0099154 A1 | 5/2004 | Raschle |
| 2004/0260265 A1 | 12/2004 | Goudaliez et al. |
| 2005/0067367 A1 | 3/2005 | Carballido |
| 2005/0115917 A1 | 6/2005 | Odet et al. |
| 2005/0124935 A1 | 6/2005 | McMichael |
| 2005/0132821 A1 | 6/2005 | Furey |
| 2005/0142315 A1 | 6/2005 | Desimone et al. |
| 2005/0167390 A1 | 8/2005 | Dubs et al. |
| 2005/0256461 A1 | 11/2005 | DiFiore et al. |
| 2006/0010991 A1 | 1/2006 | Woods et al. |
| 2006/0086758 A1 | 4/2006 | Coles |
| 2006/0272432 A1* | 12/2006 | Belongia ............... G01N 1/10 73/864.63 |
| 2007/0193375 A1 | 8/2007 | Pandori et al. |
| 2007/0290004 A1* | 12/2007 | Lee .................. B01L 3/0293 222/330 |
| 2008/0087626 A1 | 4/2008 | Tsai |
| 2008/0277926 A1 | 11/2008 | Inman et al. |
| 2008/0281200 A1 | 11/2008 | Voic et al. |
| 2009/0049988 A1 | 2/2009 | Meindl |
| 2009/0090689 A1 | 4/2009 | Walsh |
| 2009/0236374 A1 | 9/2009 | Pardes et al. |
| 2010/0065305 A1 | 3/2010 | Bernauer |
| 2010/0123094 A1 | 5/2010 | Zumbrum |
| 2010/0133459 A1 | 6/2010 | Zumbrum |
| 2010/0154569 A1 | 6/2010 | Guedon |
| 2010/0158759 A1 | 6/2010 | Olivier |
| 2010/0164176 A1 | 7/2010 | Beele |
| 2010/0183251 A1 | 7/2010 | Neltner et al. |
| 2010/0288382 A1 | 11/2010 | Levent et al. |
| 2010/0318069 A1 | 12/2010 | Hall et al. |
| 2011/0018206 A1 | 1/2011 | Beele |
| 2011/0121558 A1 | 5/2011 | Kanner |
| 2011/0155258 A1 | 6/2011 | Zumbrum |
| 2011/0155274 A1 | 6/2011 | Zumbrum |
| 2012/0064274 A1 | 3/2012 | Cai et al. |
| 2012/0074051 A1 | 3/2012 | Gebauer et al. |
| 2013/0304039 A1 | 11/2013 | Chung |
| 2014/0074015 A1 | 3/2014 | Mastri et al. |
| 2014/0076454 A1* | 3/2014 | Kjar .................. A61M 39/223 141/1 |
| 2014/0103077 A1 | 4/2014 | Zumbrum |
| 2014/0135719 A1 | 5/2014 | Jaeb et al. |
| 2014/0137519 A1* | 5/2014 | Goodwin ............... B65B 3/02 53/456 |
| 2014/0190570 A1 | 7/2014 | Zumbrum |
| 2014/0191501 A1 | 7/2014 | Brugger et al. |
| 2014/0353878 A1 | 12/2014 | Driessen et al. |
| 2015/0080814 A1 | 3/2015 | Lambert et al. |
| 2015/0114515 A1* | 4/2015 | Phallen ................. B67C 3/20 141/1 |
| 2016/0114922 A1* | 4/2016 | Boira Bonhora ......... A61J 1/10 53/426 |
| 2016/0195208 A1 | 7/2016 | Cassiday et al. |
| 2016/0199914 A1 | 7/2016 | Potter |
| 2016/0202101 A1 | 7/2016 | Sparks et al. |
| 2016/0238324 A1 | 8/2016 | Butcher et al. |
| 2016/0311674 A1 | 10/2016 | Zumbrum |
| 2016/0361488 A1 | 12/2016 | Perrenoud et al. |
| 2017/0021355 A1 | 1/2017 | Olivier et al. |
| 2017/0102089 A1 | 4/2017 | Griffin, Jr. et al. |
| 2017/0167652 A1 | 6/2017 | Snyder et al. |
| 2017/0173495 A1 | 6/2017 | Valery et al. |
| 2017/0204989 A1 | 7/2017 | Burkhart et al. |
| 2017/0219134 A1 | 8/2017 | Kedor et al. |
| 2017/0239141 A1 | 8/2017 | Davis et al. |
| 2017/0306766 A1 | 10/2017 | Munzer |
| 2018/0163898 A1 | 6/2018 | Von Arb |
| 2019/0143093 A1 | 5/2019 | Zumbrum et al. |
| 2021/0024338 A1 | 1/2021 | Zumbrum et al. |

FOREIGN PATENT DOCUMENTS

| | | |
|---|---|---|
| DE | 102014104334 | 10/2015 |
| EP | 1591517 A1 | 11/2005 |
| EP | 2802415 | 11/2014 |
| EP | 2805737 | 11/2014 |
| EP | 2144589 | 7/2016 |
| EP | 3206816 | 8/2017 |
| EP | 3215286 | 9/2017 |
| GB | 0781520 A | 8/1957 |
| JP | 2001-011126 A | 2/2001 |
| JP | 2003-125753 A | 5/2003 |
| JP | 2007-176537 A | 7/2007 |
| JP | 4466778 B1 | 5/2010 |
| JP | 2010-120250 A | 6/2010 |
| KR | 0116728 Y1 | 4/1998 |
| KR | 10-2001-0016728 A | 3/2001 |
| KR | 2017000003 * | 1/2017 |
| WO | 96/30274 A1 | 10/1996 |
| WO | WO1998/054568 A1 | 12/1998 |
| WO | 2005/084372 A2 | 9/2005 |
| WO | 2010/008396 A2 | 1/2010 |
| WO | 2012/177250 A1 | 12/2012 |
| WO | WO2013/072348 A1 | 5/2013 |
| WO | 2015/084388 A1 | 6/2015 |
| WO | WO2017/063623 A1 | 4/2017 |
| WO | WO2017/082895 A1 | 5/2017 |
| WO | WO2017/156240 A1 | 9/2017 |
| WO | WO2018/117949 A1 | 6/2018 |
| WO | WO2019/099406 A1 | 5/2019 |

OTHER PUBLICATIONS

English translation of KR 2017000003 (Year: 2017).*
International Search Report and the Written Opinion of the International Searching Authority for PCT/US2018/060828; dated Feb. 1, 2019.
International Search Report and the Written Opinion of the International Searching Authority for PCT/US2019/061229; dated Jan. 29, 2020.
Zumbrum, Michael A.; System For Simultaneous Distribution of Fluid To Multiple Vessels And Method Of Using The Same; U.S. Appl. No. 16/682,673, filed Nov. 13, 2019.
"How it's made: Silicone Hoses manufacturing by Viper Performance" (Viperperformanceuk) Oct. 1, 2014, Available Online at <https://www.youtube.com/watch?v=iuO0TdzHnWo> 5:30-6:30, 1 page.
"Saint-Gobain Biopharm C-Flex EZ Top container closures", Available Online at <http://www.biopharm.saint-gobain.com/en/products.asp?id=66>, Oct. 15, 2013.
Disposable Polyethylene Vent Cap, Corning Life Sciences Catalot, http://catalog2.corning.com/LifeSciences/en-US/Shopping/ProductsDetails.a-spx?pid . . . , known at least as early as Mar. 18, 2014, 2 pages.
GE Healthcare Life Sciences, "Disposable Cellbag bioreactors for WAVE Bioreactor systems", Data file 28-9511-36 AF, Sweden, Jun. 2012, pp. 1-12.

(56) References Cited

OTHER PUBLICATIONS

Injection-Molded Silicone Stoppers Platinum Cured, AdvantaPure, known at least as early as Jun. 6, 2011, 2 pages.
International Preliminary Report on Patentability received for PCT Patent Application No. PCT/US2018/060828, dated May 28, 2020, 10 pages.
Omnifit Solvent Safety Bottle Caps, Bio Chem Fluidics, known at least as early as Jun. 6, 2011, 16 pages.
PTFE Faced Silicone Septa for GL25 Open Top PBT Screw Cap, Corning Life Sciences Catalog, https://catalog2.corning.com/LifeSciences/en-US/Shopping/ProductDetails.a-spx?category . . . , known at least as early as Mar. 18, 2014, 1 page.
Sanl-Tech EZ Top Container Closure, Saint-Gobain Performance Plastics, known at least as early as Jun. 6, 2011, 2 pages.

\* cited by examiner

SYSTEM FOR SIMULTANEOUS FILLING OF MULTIPLE CONTAINERS

TECHNICAL FIELD

The present disclosure relates to aseptic fluid transfer assemblies, and more specifically, to a system for distributing an equal amount of fluid to multiple containers simultaneously.

BACKGROUND

Biopharmaceutical and pharmaceutical drug developers and manufacturers often develop and manufacture products in a fluid form. These products must be handled with care to maintain an aseptic environment and avoid contamination. Drugs developed and produced by biopharmaceutical and pharmaceutical companies are often produced through a multitude of steps that may require transfer of the fluids through conduits for purposes of storing, sampling, packaging, mixing, separating, or passing between stations for various steps of the manufacturing process.

The manufacturing and testing processes required by biopharmaceutical and pharmaceutical companies may require distribution of a precise amount of fluid from a large container to several smaller vessels with each vessel including the same or substantially the same amount of fluid. Typically, such distribution requires the fluid of each vessel to be measured and verified separately.

SUMMARY

This disclosure relates generally to improvements to fluid distribution systems that maintain aseptic environments while precisely distributing an equal amount fluid from a single container to multiple vessels simultaneously without the need for expensive flow sensors or control valves. In addition, in biopharmaceutical and pharmaceutical manufacturing such fluid distribution assemblies are often rendered aseptic and are intended for a single use such that maintaining a low cost can provide significant advantages. Low cost may be accomplished through reducing assembly steps, reducing filing times, reducing manufacturing steps, and/or from reducing materials used for construction. Further, filling multiple vessels simultaneously can save valuable and expensive time within a cleanroom.

In an embodiment of the present disclosure, a hub assembly is configured to distribute fluid and includes an input cap, a distribution cap, a first clamp, and a second clamp. The input cap includes a body having an inlet defined therethrough. The inlet is defined about a central axis of the hub assembly. The distribution cap is sealingly secured to the input cap with a plenum being defined between the input and distribution caps. The distribution cap includes a plurality of conduit connectors that extend from a surface of the distribution cap. Each of the conduit connectors includes an outlet that is defined therethrough and is in fluid communication with the inlet via the plenum. The plurality of conduit connectors is disposed in a ring about the central axis of the hub assembly. The first clamp is disposed over the distribution cap and is engaged with the input cap to secure the input cap to the distribution cap. The plurality of conduit connects extend through an opening of the first clamp. The second clamp is disposed over the input cap and is engaged with the distribution cap to secure the distribution cap toe the input cap. The body of the input cap extends through an opening of the second clamp. The hub assembly may include a gasket that is disposed between the input cap and the distribution cap. The gasket may seal the plenum between the input cap and the distribution cap.

In embodiments, the first clamp is rotatably fixed relative to the distribution cap and the second clamp is rotatably fixed relative to the input cap. The first clamp may include a plate in the form of a ring. The plate may receive a portion of the distribution cap therethrough. The plate may define a detent and the distribution cap may include an alignment numb. The alignment nub may be received within the detent to rotatably fix the first clamp relative to the distribution cap.

In some embodiments, the first clamp includes a plurality of fingers that extend from an outer circumference of the first clamp and towards the second clamp. The second clamp may also include a plurality of fingers that extend from an outer circumference thereof towards the first clamp with each of the plurality of fingers of the first clamp secured to the input clamp and each of the plurality of fingers of the second clamp secured to the distribution cap. The plurality of fingers of the first clamp may be arranged about the outer circumference thereof with one of the plurality of fingers of the second clamp disposed between each pair of adjacent fingers of the plurality of fingers of the first clamp.

In particular embodiments, the distribution cap includes an outer ring that encircles the plurality of conduit connectors. The first clamp may define a central opening that receives the outer ring therethrough to axially align the first clamp with the distribution cap.

In another embodiment of the present disclosure, a fluid distribution system is configured to distribute fluid from a first vessel to a plurality of secondary vessels and includes a hub assembly and a frame assembly. The hub assembly includes an input cap and a distribution cap. The input cap includes a body having an inlet defined therethrough. The inlet is defined about a central axis of the hub assembly. The distribution cap is sealingly secured to the input cap with a plenum being defined between the input and distribution caps. The distribution cap includes a plurality of conduit connectors that extend from a surface of the distribution cap. Each of the conduit connectors includes an outlet that is defined therethrough and is in fluid communication with the inlet via the plenum. The plurality of conduit connectors is disposed in a ring about the central axis of the hub assembly. The frame assembly supports the hub assembly with the central axis of the hub assembly coaxially aligned with a central axis of the frame assembly. The frame assembly is configured to secure each of the secondary vessels a predetermined distance relative to the hub assembly.

In some embodiments, the hub assembly includes a first clamp and a second clamp. The first clamp may be disposed over the distribution cap and be engaged with the input cap to secure the input cap to the distribution cap. The plurality of conduit connects may extend through an opening of the first clamp. The second clamp may be disposed over the input cap and be engaged with the distribution cap to secure the distribution cap to the input cap. The body of the input cap may extend through an opening of the second clamp.

In embodiments, the fluid distribution system includes a plurality of distribution conduits that each include a first end that is sealingly secured to a respective conduit connector of the plurality of conduit connectors of the distribution cap. A distribution lumen defined by each of the distribution conduits in fluid communication with the plenum through the outlet of the respective conduit connector. Each distribution conduit may include a coupling that is secured within a second end opposite the first end. The coupler may be configured to be received within an inlet conduit of a respective secondary vessel.

In some embodiments, the fluid distribution system includes a plurality of secondary vessels. Each of the secondary vessels may include an inlet conduit that is in fluid communication with the plenum through respective distribution conduit of the plurality of distribution conduits. Each inlet conduit and respective distribution conduit may form an output tube between the respective conduit connector and a respective secondary vessel. Each output tube may form an arc between the respective conduit connector and the respective secondary vessel. The arc may be tuned to balance a flow rate of a fluid from the hub assembly between the output tubes.

In certain embodiments, the fluid distribution system includes an input tube that has a first end sealingly secured to the input cap and that defines an input lumen in fluid communication with the plenum through the inlet. The input tube may have a second end that is configured to be secured to the primary vessel. The second end of the input tube may include an aseptic connector to couple to the primary vessel. The fluid distribution system may include a pump that is disposed about the input tube. The pump may be configured to pump fluid from the primary vessel and into the plenum of the hub assembly through the input tube. Additionally or alternatively, the primary vessel may be pressurized to feed the fluid into the inlet.

In particular embodiments, the frame assembly includes a support collar, lower arms, and a vessel collar. The support collar may support and coaxially align the hub assembly with the central axis of the frame assembly. The support collar may define the central axis of the frame assembly. Each of the lower arms may extend between the support collar and a joint. The vessel collar may be secured to at each joint. Additionally, the vessel collar may be releasably secured at each joint.

In embodiments, the vessel collar includes an outer ring, arm nodes, and vessel receivers. Each arm node may extend inward from the outer ring and be configured to secure to a joint of a respective lower arm. Each vessel receiver may extend inward from the outer ring, define an entry at the outer ring, and be configured to secure the secondary vessels to the vessel collar. The frame assembly may include upper arms and a central hub. Each of the upper arms may extend from a respective joint to the central hub. The central hub may be disposed about the central axis and offset from the support collar along the central axis.

In another embodiment of the present disclosure, a method of aseptically distributing fluid from a first vessel to a plurality of secondary vessels includes securing each of the secondary vessels a predetermined distance form a hub assembly and flowing a fluid through an input tube from the first vessel into a plenum of the hub assembly. A plurality of output tubes extends from the hub assembly with each output tube extending between the hub assembly and a respective one of the secondary vessels. Each output tube forms a predetermined arc between the hub assembly and the respective secondary vessel. The flow of fluid into the plenum of the hub assembly moves from the plenum through each of the output tubes such that an equal amount of fluid flows from the plenum into each of the secondary vessels simultaneously.

In embodiments, flowing the fluid through the input tube includes activating a pump to flow the fluid through the input tube at a predetermined flow rate. Activating the pump may include increasing a pressure of fluid within the input tube from the first vessel to the hub assembly.

In some embodiments, flowing fluid through the input tube includes flowing fluid from the plenum through each of the output tubes ±1% of an amount of fluid into each of the secondary vessels. The secondary vessels may be bottles or bags.

In certain embodiments, the method includes reversing fluid flow such that an equal amount of fluid is simultaneously drawn from each of the secondary vessels into the primary vessel.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Exemplary embodiments of this disclosure are described below and illustrated in the accompanying figures, in which like numerals refer to like parts throughout the several views. The embodiments described provide examples and should not be interpreted as limiting the scope of the invention. Other embodiments, modifications, and improvements of the described embodiments will occur to those skilled in the art and all such other embodiments, modifications, and improvements are within the scope of the present invention. Features from one embodiment or aspect may be combined with features from any other embodiment or aspect in any appropriate combination. For example, any individual or collective features of method aspects or embodiments may be applied to apparatus, product, or component aspects or embodiments and vice versa.

Figure 1:
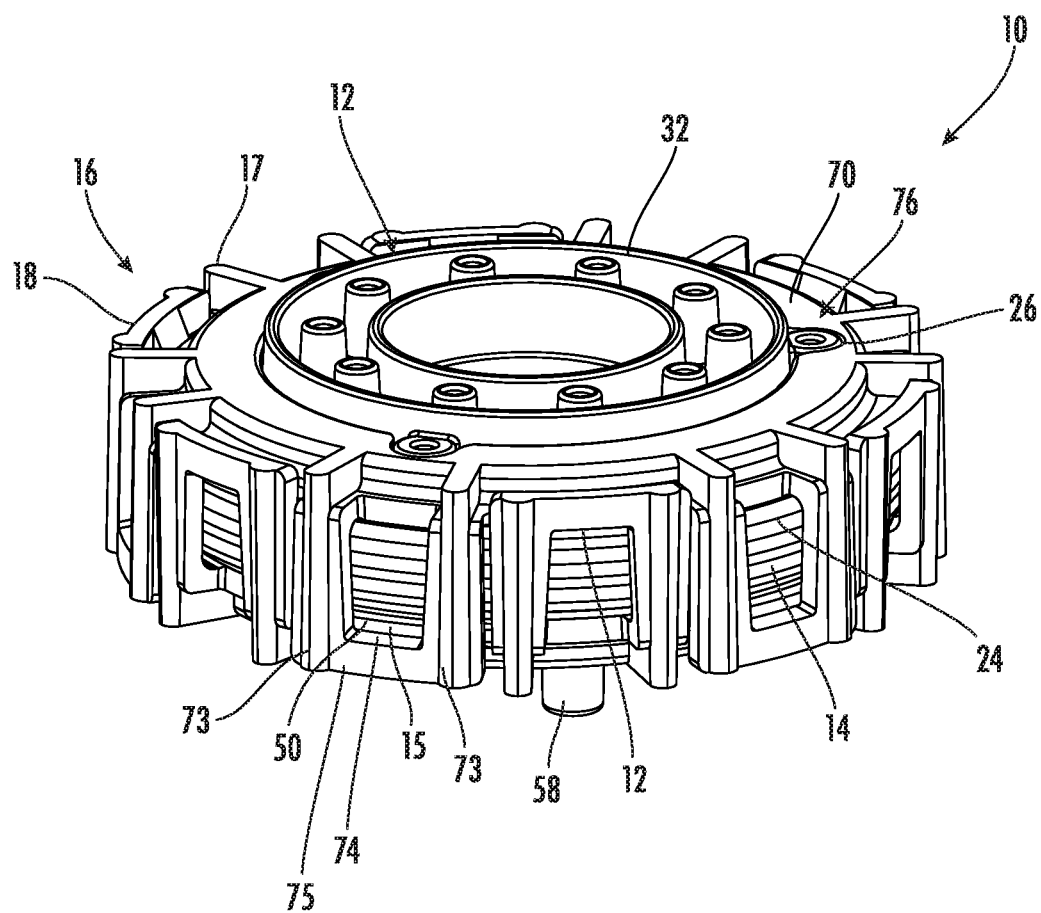
FIG. 1 is a perspective view of an exemplary hub assembly provided in accordance with the present disclosure.
Figure 2:
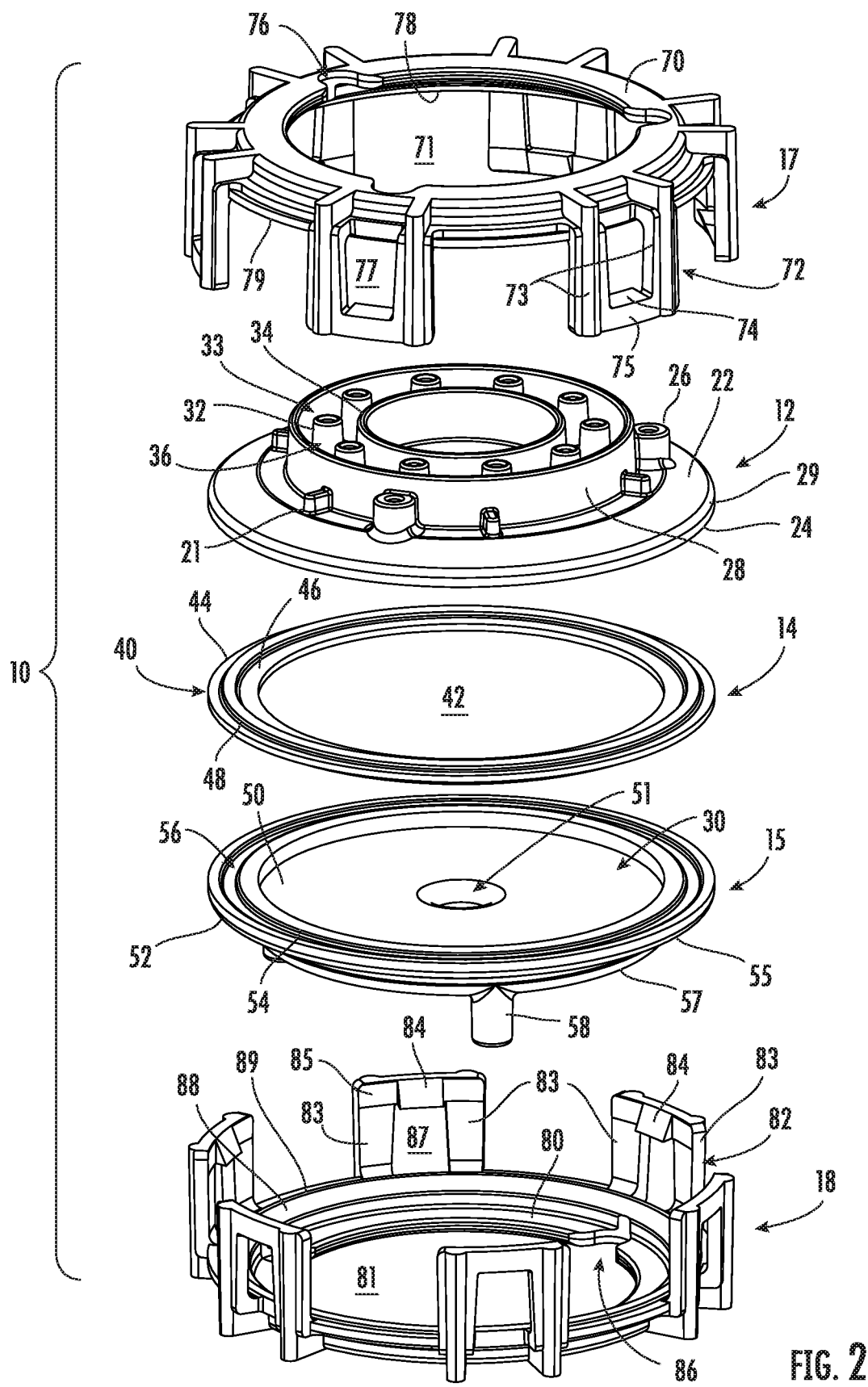
FIG. 2 is a perspective view, with parts separated, of the hub assembly of FIG. 1.

Referring to FIGS. 1 and 2, an exemplary hub assembly 10 for distributing flow through an inlet 51 to a plurality of outlets 33 is provided in accordance with the present disclosure. The hub assembly 10 includes an upper or distribution cap 12, a lower or input cap 15, a gasket 14, and a hub clamp 16 having an upper clamp 17 and a lower clamp 18. The hub assembly 10 is releasably secured together by the hub clamp 16. The upper clamp 17 is clamped to the input cap 15 and the lower clamp 18 is clamped to the distribution cap 12 such that the gasket 15 is compressed between the caps 12, 15.

Figure 3:
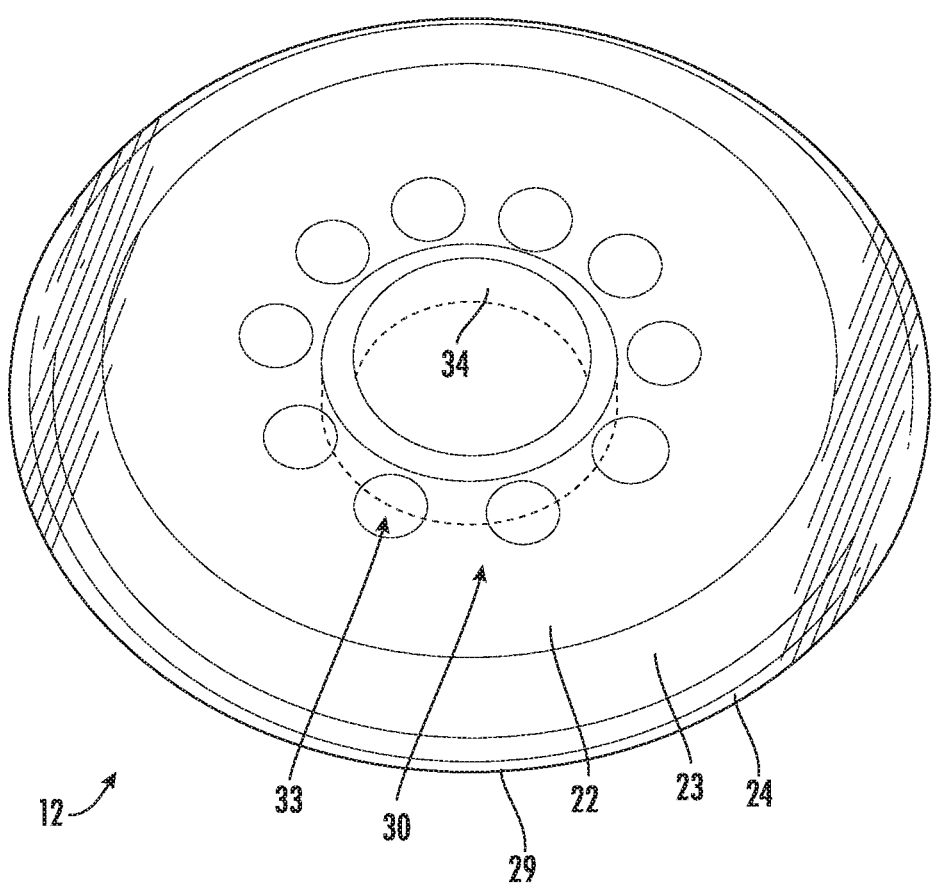
FIG. 3 is a bottom perspective view of a distribution cap of the hub assembly of FIG. 1.

With additional reference to FIG. 3, the distribution cap 12 has an annular body 22 in the form of a disc. The body 22 includes an annular outer rim 24 that extends downward from the body 22 and an annular inner rim 23 that extends downward from the body 22 to define a groove 25 between the inner and outer rims 23, 24. The upper surface of the groove 25 may be defined by a lower surface of the body 22. The outer rim 24 may extend downward from the outer extremity of the body 22 or may be spaced apart from the outer extremity of the body 22 such that the body 22 extends beyond the outer rim 24. The inner rim 23 defines an upper portion of a plenum 30 with a diameter of the plenum 30 determined by a diameter of the inner rim 23 and a height of the upper portion of the plenum 30 defined by the downward extension of the inner rim 23 from the body 22.

The distribution cap 12 also includes a plurality of outlet conduit connectors 32 that extend from an upper surface of the body 22. Each of the outlet conduit connector 32 define an outlet 33 that extends through the outlet conduit connect 32 and into the plenum 30. The outlet conduit connectors 32 are spaced about a central axis of the body 22 and define an outlet ring about the central axis of the body 22. The outlet conduit connectors 32 are radially spaced apart from one another and may be radially spaced apart from one another equal distances, e.g., $2\pi/n$ with n being the number of outlet conduit connectors 32. Alternatively, the outlet conduit connectors 32 may be radially spaced apart from one another unequal distances. As shown, a central axis of each of the outlets 33 extends in a direction parallel to the central axis of the body 22. In some embodiments, the central axis of each of outlets 33 may extend at an angle to the central axis of the body 22. For example, the central axis of each of the outlets 33 may be angled towards or away from the central axis of the body 22 by a predetermined angle with a radius of the outlet ring intersecting the central axis of the outlet 33 and/or the central axis of each of the outlets 33 may be angled relative to a tangent of the of the outlet ring intersecting the central axis of the outlet 33. The outlet conduit connectors 32 may be positioned in an annular recess 36 that is defined between an annular outer wall 28 and an annular inner wall 34 that each extend from an upper surface of the body 22.

The distribution cap 12 may also include one or more alignment nubs 26 that extend from the upper surface of the body 22. The alignment nubs 26 may be positioned between the outer wall 28 and the outer extremity of the body 22. The alignment numbs 26 may be positioned about the body 22 to form a ring about the central axis of the body 22. The distribution cap 12 may include three alignment nubs 26 that are radially spaced about the body 22 an equal distance from one another, e.g., $2\pi/3$ apart, or may be unequally spaced apart from one another. The body 22 may also define a ledge 24 adjacent the outer extremity of the body 22. The ledge 24 may be positioned above the outer rim 28 and have an upper surface below the upper surface of the remainder of the body 22. The upper surface of the ledge 24 may be positioned between the upper and lower surfaces of the body 22 or may be positioned at the lower surface of the body 22. The upper surface of the ledge 24 may provide a clamping surface for the lower clamp 18. In some embodiments, the distribution cap 12 includes one or more risers 21 that extend from the upper surface of the body 22 and extend outward from the outer wall 28. The risers 21 extend from the upper surface of the body 22 to a lesser extent than the alignment nubs 26 extend from the upper surface of the body 22. The risers 21 may be positioned above or aligned with the inner rim 23 such that downward pressure on the risers 21, e.g., a clamping force, may be transferred to the inner rim 23. The risers 21 are radially spaced an equal distance from one another about the central axis of the body 22.

Continuing to refer to FIGS. 1 and 2, the input cap 15 includes an annular body 50 in the form of a disc and defines the inlet 51 that extends through the body 52 about a central axis of the body 50. The body 50 includes an annular outer rim 52 and an annular inner rim 54 that extend from an upper surface of the body 50 to define an annular groove 56 therebetween. The outer rim 52 may extend upward from the outer extremity of the body 50 or may be spaced apart from the outer extremity of the body 50 such that the body 50 extends beyond the outer rim 52. The inner rim 54 defines a lower portion of the plenum 30 with a diameter of the plenum 30 determined by a diameter of the inner rim 54 and a height of the lower portion of the plenum 30 is defined by the upward extension of the inner rim 54 from the body 50. The outer rim 52 may have a diameter similar to the outer rim 24 of the distribution cap 12 and the inner rim 54 may have a diameter similar to the inner rim 23 of the distribution cap 12 such that the grooves 25, 56 may have similar dimensions.

The body 50 of the input cap 15 may include an outer wall 57 and/or one or more alignment nubs 58 that extend from a lower surface of the input cap 15 opposite the upper surface of the input cap 15. The outer wall 57 is similar to the outer wall 28 of the distribution cap 12 and may have a diameter similar to the outer wall 28. The alignment nubs 58 may be similar to the alignment nubs 26 of the distribution cap 12 and may be positioned at a similar radius to the alignment nubs 26. In addition, the input cap 15 may include three alignment nubs 58 that are radially spaced about the body 50 an equal distance from one another, e.g., $2\pi/3$ apart, or may be unequally spaced apart from one another. The body 50 may also define a ledge 55 adjacent the outer extremity of the body 50. The ledge 55 may be positioned below the outer rim 52 and have a lower surface above the lower surface of the remainder of the body 50. The lower surface of the ledge 55 may be positioned between the upper and lower surfaces of the body 50 or may be positioned at the upper surface of the body 50. The lower surface of the ledge 50 may provide a clamping surface for the upper clamp 17. The input cap 15 may also include risers (not shown) similar to risers 21 detailed above with respect to the distribution cap 12.

The distribution cap 12 and the input cap 15 may be molded, formed from an additive manufacturing process, thermoforming process, casting process, or injection molding process. For example, each of the caps 12, 15 may be three-dimensionally printed. Each of the caps 12, 15 may be monolithically formed. In some embodiments, the caps 12, 15 may be sterilized after being packaged for shipping. For example, gamma irradiation can be used to terminally sterilize the entire product assembly and packaging material.

With particular reference to FIG. 2, the gasket 14 is configured to provide a seal between the distribution cap 12 and the input cap 15 such that the plenum 30 is defined therebetween. The gasket 14 includes an annular body 40 that defines a central opening 42 passing therethrough about a central axis of the body 40. The body 40 includes an outer flange 44, an inner flange 46, and an annular rib 48 positioned between the outer and inner flanges 44, 46. The rib 48 is configured to be received and/or compressed within the grooves 25, 56 of the distribution cap 12 and the input cap 15. Specifically, the rib 48 extends above and below the outer and inner flanges 44, 46. The rib 48 may extend above and below the outer and inner flanges 44, 46 a height substantially equal to or greater than a depth of the grooves 25, 56 of the distribution cap 12 and the input cap 15, respectively. The thickness of the rib 48 when measured along a radius of the gasket 14 is substantially equal to a width of the grooves 25, 56 of the distribution cap 12 and the input cap 15 when measured along a radius of the respective cap 12, 15. Dimensions of the grooves 25, 56 and the rib 48 may comply with ASME BPE 2009 standards for hygienic unions.

The outer flange 44 extends outward from the rib 48 and is configured to be compressed between the outer rim 24 of the distribution cap 12 and the outer rim 52 of the input cap 15. The outer flange 44 may extend from the rib 48 a distance equal to a thickness of the outer rims 24, 52 when measured along a radius of the respective cap 12, 15. The inner flange 46 extends inward form the rib 48 and is configured to be compressed between the inner rim 23 of the distribution cap 12 and the inner rim 54 of the input cap 15. The inner flange 46 may extend from the rib 48 a distance equal to a thickness of the inner rims 23, 54 when measured along a radius of the respective cap 12, 15. The central opening 42 may define a central portion of the plenum 30 between the upper and lower portions of the plenum 30. The gasket 14 is formed of an aseptic compressible material that is capable of forming a seal between the distribution cap 12 and the input cap 15. The gasket 14 may be formed of a variety of materials including, but not limited to, copolymers of acrylonitrile and butadiene (BUNA-N), VITON™, fluoroelastomers as defined by ASTM D1418 (FKM), ethylene propylene diene monomer (EPDM), polytetrafluoroethylene (PTFE), silicone (VMQ), phenyl silicone (PMVQ), and others. In some embodiments, the gasket may be overmolded onto the distribution cap 12 or the input cap 15. The gasket 14 is illustrated as an open gasket, but other types of gaskets are available that may be used within the hub assembly 10. For example, the gasket 14 may be an orifice gasket, a screen gasket, and a perforated plate gasket that may control flow of a fluid through the hub assembly 10, or provide a filtering function. Each of these alternative gaskets are available in several sizes, or can be customized, based upon the dimensions of the fittings, the orifice diameter through the gasket, or the pore size of the perforated plate or screen gaskets. Suitable gaskets are available from Newman Sanitary Gasket Company, Flow Smart Inc., and others.

For addition details of similar distribution caps, input caps, and gaskets, reference may be made to U.S. Patent Publication No. 2018/0297753, the entire contents of which are hereby incorporated by reference.

With continued reference to FIGS. 1 and 2, the upper and lower clamps 17, 18 of the hub clamp 16 are substantially similar to one another with like elements labeled with similar labels, e.g., elements of the upper clamp 17 are labeled with a preceding "7" and elements of the lower clamp are labeled with a preceding "8", such that the structure of each of the upper and lower clamps 17, 18 with be described with respect to the lower claim 18. The description of the lower clamp 18 below includes references to elements of the distribution cap 12 and the input cap 15, these references are reversed with respect to the upper clamp 17 as will be appreciated below when the assembly of the hub assembly is described in detail. In addition, the orientation of the upper clamp 17 is flipped and rotated about the central axis thereof relative to the orientation of the lower clamp 18.

The lower clamp 18 includes an annular plate 80 and a clamp ring 88. The plate 80 includes a clamping surface that is configured to oppose the plate 70 of the upper clamp 17. The clamping surface of the plate 80 is within and offset from the clamp ring 88 such that a clamping surface of the clamp ring 88 is above clamping surface of the plate 80. The offset of the clamping surface of the plate 80 and the clamping surface of the clamp ring 88 may be substantially equal to the height of risers of distribution or input caps 12, 15, e.g., risers 21. The plate 80 may engage risers (not shown) of the input cap 12 to urge inner rim 54 of input cap 12 towards the distribution cap 15. In embodiments where the input cap 12 does not include risers, the plate 80 may be positioned above a lower surface of the body 50. The clamping surface of the clamp ring 88 may have a width along a radius of the lower clamp 18 equal to a lower surface of the body 50 of the input cap 15 that extends outward from the alignment nubs 58. The clamp ring 88 is configured to engage the body 50 of the input cap 15 to urge the input cap 15 towards the distribution cap 12. The lower clamp 18 may include an alignment ring 89 that extends upward from the clamp ring 88 at an outer circumference thereof and is configured to be received within the ledge 55 of the input cap 15 to coaxially align the lower clamp 18 with the input cap 15.

The plate 80 defines a central opening 81 that is dimensioned to receive the outer wall 57 of input cap 15 to coaxially align the lower clamp 18 with the input cap 15. The plate 80 also defines one or more detents 86 adjacent the central opening 81. The detents 86 may extend through the plate 80 and/or may be in communication with the central opening 81. Each of the detents 86 is configured to receive one of the alignment nubs 58 of the input cap 15 to radially align the lower clamp 18 with the input cap 15. In some embodiments, the plate 80 includes an equal number of detents 86 to the number of alignment nubs 58 of the input cap 15. In other embodiments, the plate 80 includes greater number of detents 86 to the number of alignment nubs 58 of the input cap 15.

The lower clamp 18 includes a number of fingers 82 configure to extend towards the upper clamp 17 and engage the distribution cap 12. Each of the fingers 82 extend from an outer circumference of the clamp ring 88 in a direction away from the plate 80. The fingers 82 are radially spaced about the outer circumference of the clamp ring 88 and configured to engage the distribution cap 12 to maintain a plane of the body 22 of the distribution cap 12 parallel to a plane of the plate 80 and/or to apply equal pressure about the plane of the body 22. Each finger 82 defines a space between adjacent fingers 82 which is sized to allow an opposing finger 72 of the upper clamp ring 17 to be received therein. Each finger 82 includes a pair of legs 83 that extend from the outer circumference of the clamp ring 88 to an end spaced apart from the clamp ring 88. The pair of legs 83 support a bridge 85 that connects ends of the legs 83 spaced apart from the clamp ring 88. The bridge 85 supports a protuberance or lip 84 that extends from the bridge 85 towards the central axis of the lower clamp 18. The fingers 82 are biased inward such that the bridges 85 are biased towards the central axis of the lower clamp 18.

Each lip 84 is configured to engage a surface of the distribution cap 12 and prevent the distribution cap 12 from moving away from the lower clamp 18. In some embodiments, the lip 84 engages an upper surface of the ledge 29 of the distribution cap 12. The lip 84 may be wedge shaped such that as the lip 84 engages the distribution cap 12, the fingers 82 are urged outward and away from the distribution cap 12 until a clamping surface of the lips 84 are positioned above the surface of the distribution cap 12, e.g., the upper surface of the ledge 29. When the clamping surface of a respective lip 84 is positioned above the surface of the distribution cap 12, the finger 82 may bias the lip 84 towards the central axis of the lower clamp 18 such that the clamping surface of the lip 84 is positioned above and/or engaged with the upper surface of the distribution cap 12 to retain the distribution cap 12 relative to the lower clamp 80.

Continuing to refer to FIGS. 1 and 2, the assembly of the hub assembly 10 is described in accordance with the present disclosure. Initially, the gasket 14 is positioned relative to one of the caps 12, 15 such that the rib 48 is received within a respective one of the grooves 25, 56. With the rib 48 received within a respective one of the grooves 25, 56, the other one of the caps 12, 15 is positioned over the gasket 14 such that the rib 48 is received in the other one of the grooves 25, 56. With the rib 48 received in each of the grooves 25, 56, the inner flange 46 of the gasket 30 is positioned between the inner rims 23, 54 of the caps 12, 15 and the outer flange 44 of the gasket 30 is positioned between the outer rims 24, 52 of the caps 12, 15 such that the gasket 30 forms a seal between the caps 12, 15. With the gasket 30 forming a seal between the caps 12, 15, the caps 12, 15 define the plenum 30 therewithin between the inner rims 23, 54 and the bodies 22, 50.

With the gasket 14 positioned between the caps 12, 15, the hub clamp 16 is assembled over the caps 12, 15. As detailed below, the lower clamp 18 is secured to the caps 12, 15 before the upper clamp 17; however, this may be reversed with the upper clamp 17 being secured to the caps 12, 15 before the lower clamp 18. In some embodiments, the upper and lower clamps 17, 18 may be secured to the caps 12, 15 simultaneously.

To secure the lower clamp 18 to the caps 12, 15, the lower clamp 18 is positioned with the plate 80 positioned about the outer wall 57 of the input cap 15 and the fingers 82 extending towards the distribution cap 12. As the plate 80 approaches the outer wall 57, the fingers 82, and in particular the lips 84, may engage the outer circumference of the input cap 15, the gasket 14, and/or the distribution cap 12 which may urge the fingers 82 outward, e.g., away from the central axis of the lower clamp 18. Interaction of the outer wall 57 of the input cap 15 and the plate 80 of the lower clamp 18 and/or interaction of the ledge 55 of the input cap 15 and the alignment ring 89 of the lower clamp 18 axially aligns the lower clamp 18 with the input cap 15 such that the lower clamp 18 and the input cap 15 are coaxially aligned with one another. In addition, engagement of the fingers 82 with the outer circumference of the input cap 15, the gasket 14, and/or the distribution cap 12 may axially align the lower clamp 18 with the input cap 15. With the lower clamp 18 coaxially aligned with the input cap 15, the lower clamp 18, or the input cap 15, is rotated until the alignment nubs 58 of the input cap 15 are aligned with the detents 86 of the lower clamp 18 such that the lower clamp 18 is rotationally or radially aligned with the input cap 15. With the input cap 15 radially aligned with the lower clamp 18, the distribution cap 12 is pressed into the lower clamp 18 until the lips 84 engage the ledge 29 of the outer rim 24 of the distribution cap 12 to secure the distribution cap 12 to the lower clamp 18. When the lips 84 engage the ledge 29, the lower clamp 18 is secured to the input cap 15 with the gasket 40 compressed between the caps 12, 15 to form a seal therebetween. The engagement of the lips 84 and the ledge 29 also secures the input cap 15 to the lower clamp 18 with the body 50 of the input cap 15 engaging the plate 80 of the lower clamp 18. In addition, when the lips 84 engage the ledge 29, portions of the body 50 of the input cap 15 may extend through the central opening 81 of the lower clamp 18, e.g., the alignment ring 57 or the alignment nubs 58.

With the lower clamp 18 secured to the caps 12, 15, the upper clamp 17 is secured to the caps 12, 15. To secure the upper clamp 17 to the caps 12, 15, the upper clamp 17 is positioned with the plate 70 positioned about the outer wall 28 of the distribution cap 12 and the fingers 72 extending towards the input cap 15. As the plate 70 approaches the outer wall 28, the fingers 72, and in particular the lips 74, may engage the outer circumference of the distribution cap 12, the gasket 14, and/or the input cap 15 which may urge the fingers 72 outward, e.g., away from the central axis of the upper clamp 17. Interaction of the outer wall 28 of the distribution cap 12 and the plate 70 of the upper clamp 17 and/or interaction of the ledge 29 of the distribution cap 12 and the alignment ring 79 of the upper clamp 17 axially aligns the upper clamp 17 with the distribution cap 12 such that the upper clamp 17 and the distribution cap 12 are coaxially aligned with one another. In addition, engagement of the fingers 72 with the outer circumference of the distribution cap 12, the gasket 14, and/or the input cap 15 may axially align the upper clamp 17 with the distribution cap 12. With the upper clamp 17 coaxially aligned with the distribution cap 12, the distribution cap 12 is rotated until the alignment nubs 26 of the distribution cap 12 are aligned with the detents 76 of upper clamp 17 such that the upper clamp 17 is rotationally or radially aligned with the distribution cap 12. The engagement of the lower clamp 18 with the distribution cap 12 may make it difficult to rotate the distribution cap 12 when the lower clamp 18 is engaged therewith. In some embodiments, the upper clamp 17 may be disposed over the distribution cap 12 before the lower clamp 18 is engaged with the distribution cap 12 to radially align the upper clamp 17 with the distribution cap 12 during radial alignment of the lower clamp 18 with the input cap 15. With the distribution cap 12 radially aligned with the upper clamp 17, each finger 72 of the upper clamp 17 is positioned between adjacent fingers 82 of the lower clamp 18 and each finger 82 of the lower clamp 18 is positioned between adjacent fingers 72 of the upper cap 17. When the distribution cap 12 is radially aligned with the distribution cap 12, the input cap 15 is pressed into the upper clamp 17 until the lips 74 engage the ledge 55 of the outer rim 52 of the input cap 15 to secure the input cap 15 to the upper clamp 17. When the lips 74 engage the ledge 55, the upper clamp 17 is secured to the input cap 15 with the gasket 40 compressed between the caps 12, 15 to form a seal therebetween. The engagement of the lips 74 and the ledge 55 also secures the distribution cap 12 to the upper clamp 17 with the body 22 of the distribution cap 12 engaging the plate 70 of the upper clamp 17. In addition, when the lips 74 engage the ledge 55, portions of the body 22 of the distribution cap 12 may extend through the central opening 71 of the upper clamp 17, e.g., the inner wall 34, the outer wall 58, or the conduit connectors 32. With each clamp 17, 18 secured to the respective cap 12, 15, the hub assembly 10 is formed with the hub clamp 16 securing the caps 12, 15 together such that the gasket 40 forms a seal between the caps 12, 15.

When the hub clamp 16 is secured to the caps 12, 15, the plates 70, 80 of the clamps 17, 18 may engage risers, e.g., risers 21, of the caps 12, 15 to apply pressure to the inner flange 46 of the gasket 40 and the clamp rings 78, 88 of the clamps 17, 18 may engage the caps 12, 15 outside of the alignment nubs 26, 58 to apply pressure to the outer flange 48 of the gasket 40. The pressure on the inner and outer flanges 46, 48 improve the seal formed by the flange 40 between the caps 12, 15. For example, a desired pressure profile may be established across the seal from an inner edge of the inner flange 44 to an outer edge of the outer flange 46. In addition, when the hub clamp 16 is secured to the caps 12, 15, each of the clamps 17, 18 independently secures the caps 12, 15 to one another and maintains the seal between the caps 12, 15 Further, when the hub clamp 16 is secured to the caps 12, 15, the fingers 72 of the upper clamp 17 engage the input cap 15 to urge the input cap 15 upward in between the fingers 82 of the lower clamp 18 that engage the distribution cap 12 to urge the distribution cap 12 downward which alternates the pressure on the gasket 40 to improve the seal formed between the caps 12, 15.

In some embodiments, the hub assembly 10 is assembled by positioning one of the caps 12, 15 within a central opening 71, 81 of the one of the clamps 17, 18; positioning the rib 48 of the gasket 40 within the groove 25, 56 of the one of the caps 12, 15; positioning the other cap 12, 15 over the gasket 40 with the rib 48 received within the respective groove 25, 56; and positioning the other clamp 17, 18 over the other cap 12, 15 to form the hub assembly 10. The clamps 17, 18 may be pressed together over the caps 12, 15 or may be sequentially secured to the respective cap 12, 15 as detailed above.

In certain embodiments, the hub assembly 10 is assembled without the clamp assembly 16 including the clamps 17, 18. For example, the hub assembly 10 may be assembled with a single clamp, e.g., a single pin hygienic clamp. Alternatively, the caps 12, 15 may be secured together with an adhesive bond, overmolding, or by welding, e.g., ultrasonic welding, the caps 12, 15 to one another. In some embodiments, the gasket 40 may adhesively secure the caps 12, 15 to one another. In particular embodiments, the gasket 40 may be adhered or attached to one or both of the caps 12, 15.

Figure 4:
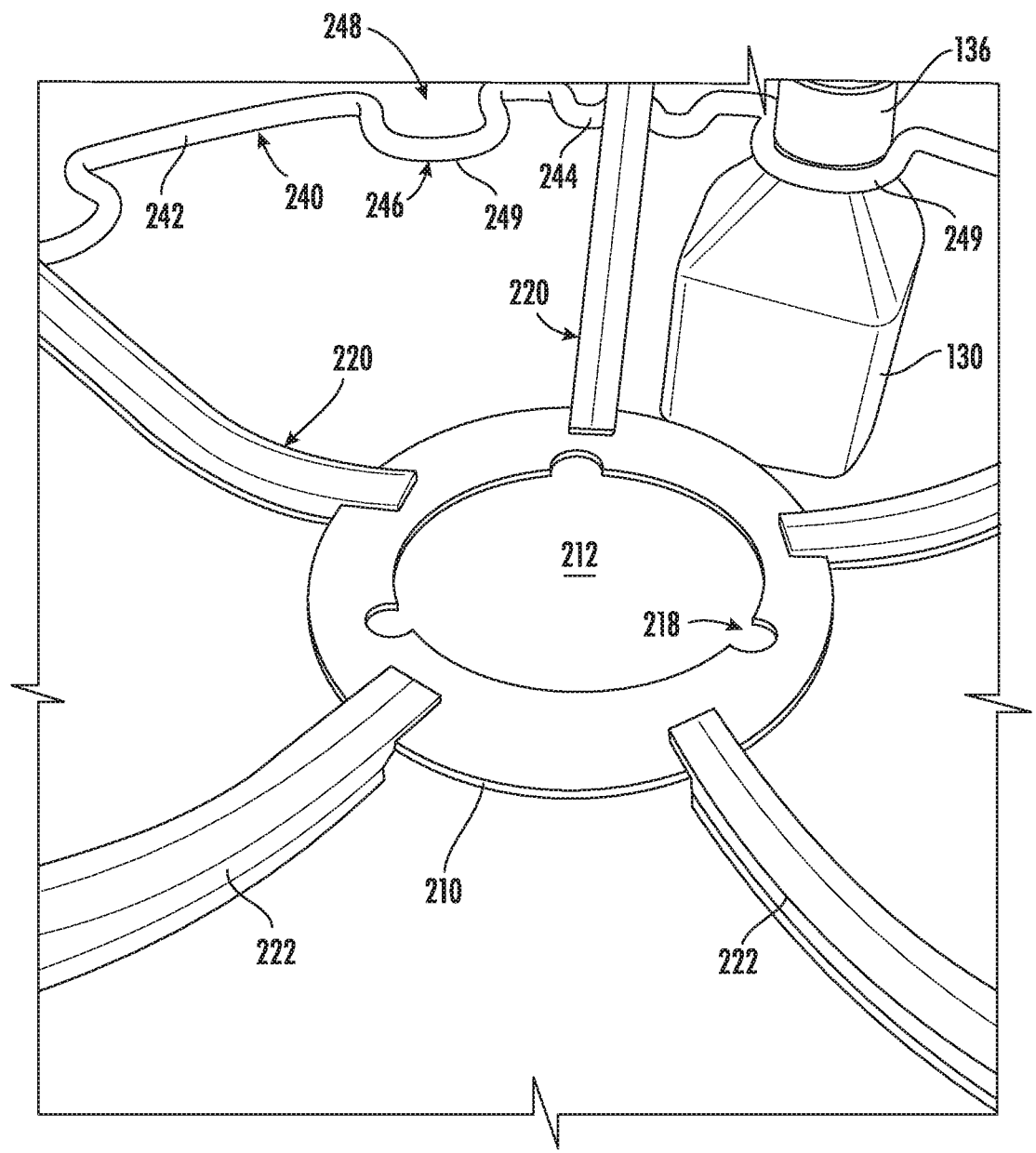
FIG. 4 is a perspective view of an exemplary frame assembly provided in accordance with the present disclosure including the hub assembly of FIG. 1.
Figure 5:
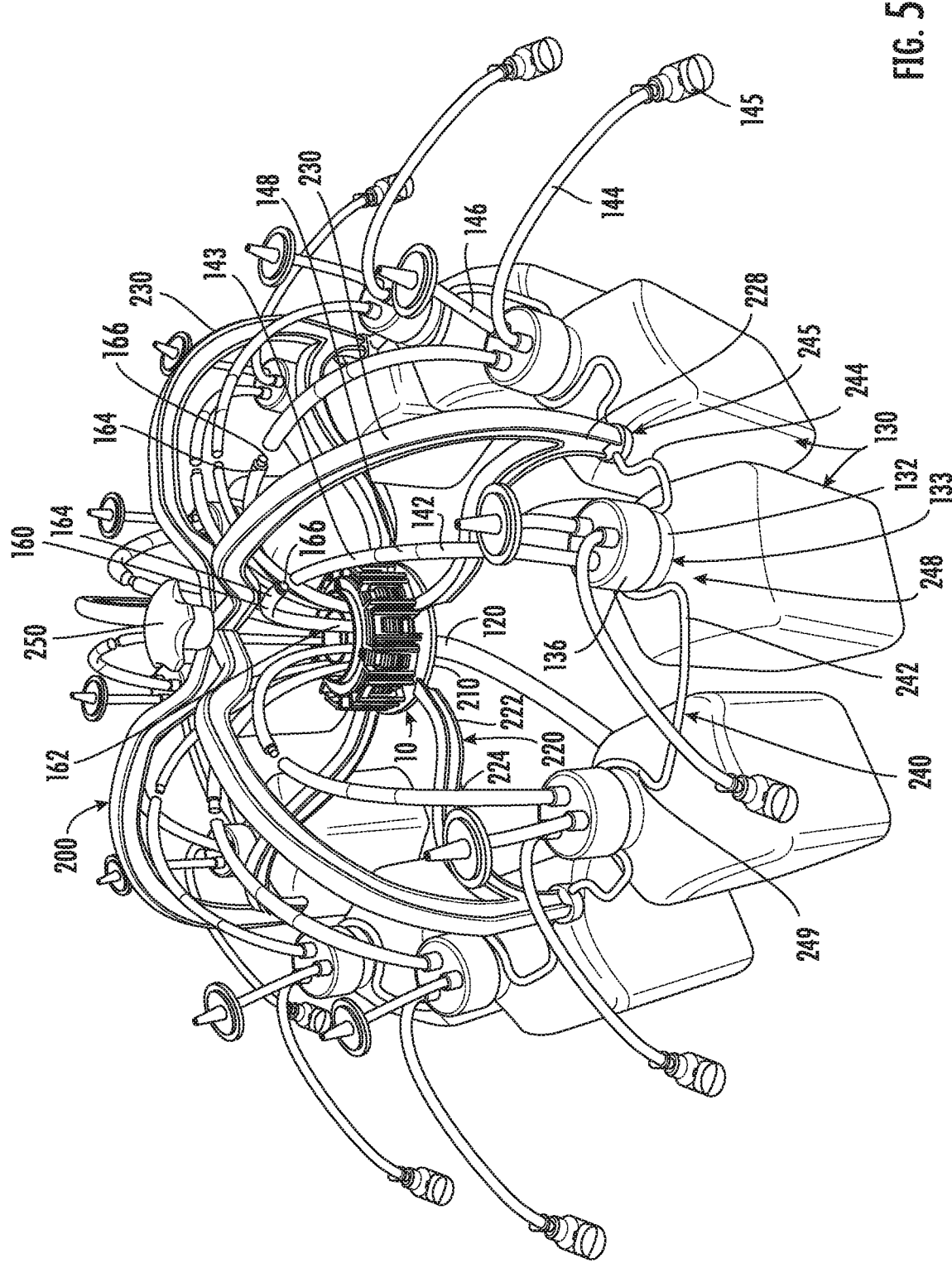
FIG. 5 is a perspective view of an exemplary fluid distribution system provided in accordance with the present disclosure including the frame assembly of FIG. 4 and the hub assembly of FIG. 1.
Figure 6:
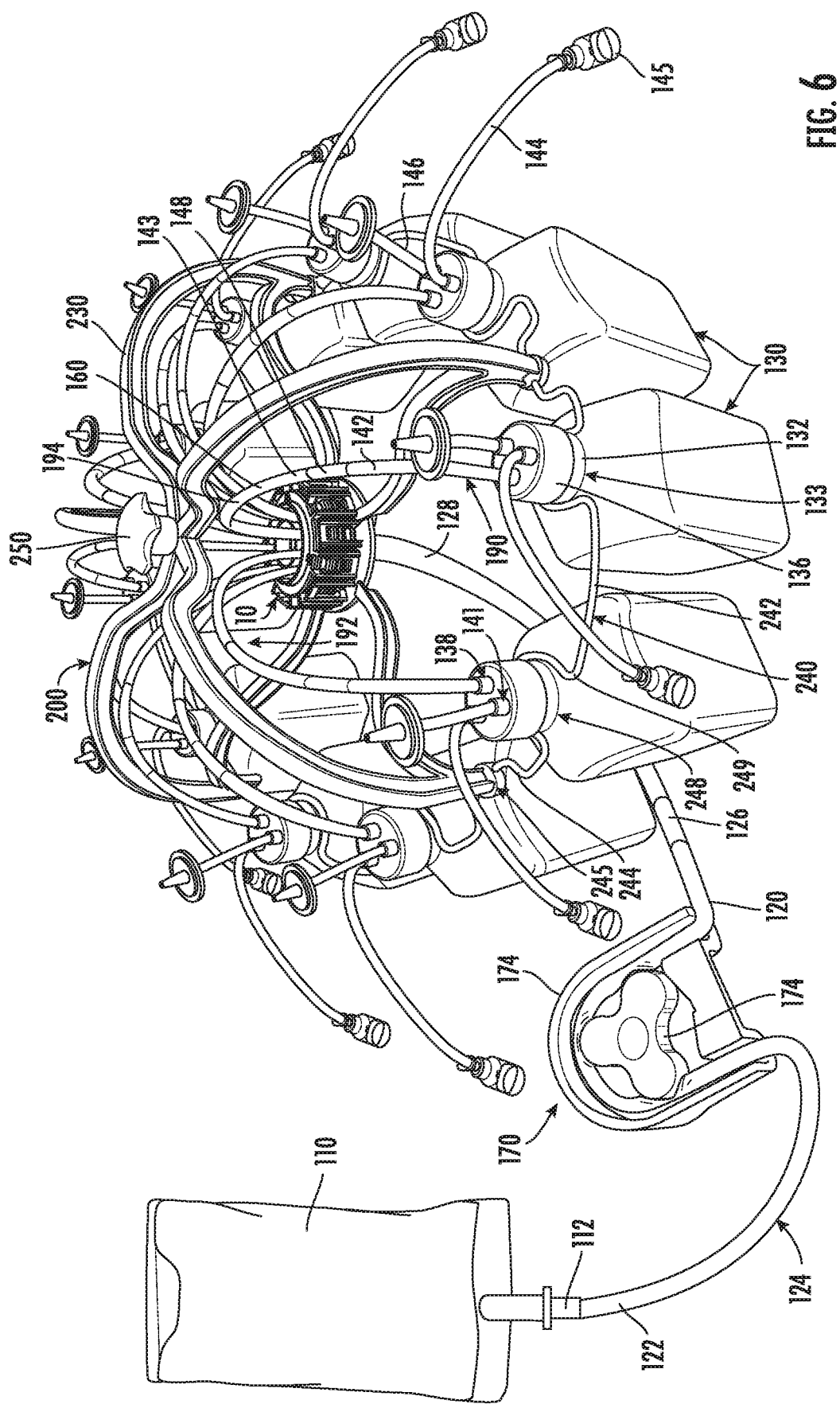
FIG. 6 is a perspective view of the fluid distribution system according to FIG. 5 with a first vessel and a pump.

With reference to FIGS. 4-6, a fluid distribution system 1 for distributing a fluid from a primary vessel 110 to plurality of secondary vessels 130 is provided in accordance with the present disclosure. The fluid distribution system 1 includes the hub assembly 10, an input conduit 120, distribution conduits 160, and a frame assembly 200.

With particular reference to FIG. 5, the primary vessel 110 includes a fluid to be distributed in equal amounts, ±1%, to each one of the secondary vessels 130. The primary vessel 110 may be a rigid vessel, e.g., a bottle, or flexible vessel, e.g., a collapsible bag. The primary vessel 110 may be positioned above, below, or level with the hub assembly 10 and may be oriented with an opening 112 oriented downwards or oriented upwards. For example, the primary vessel 110 may be suspended from a hanger above hub assembly 10. In addition, the primary vessel 110 may be sealed or may be vented. In some embodiments, the primary vessel 110 is vented with an aseptic hydrophobic vent to prevent contamination of a liquid contained therewithin.

The primary vessel 110 is connected to the hub assembly 10 via the input conduit 120. The input conduit 120 includes a first terminus or end 122 and a second terminus or end 129, and defines an input lumen 124 therethrough. The first end 129 of the input conduit 120 may be connected to the primary vessel 110 by any known means including a barb connection, a luer connection, a nipple connection, a needle connection, etc. For example, the first end 129 may be fitted with an aseptic connector to couple to the primary vessel 110. A suitable aseptic connector is commercially available from Sartorius as an Opta® Sterile Connector. In some embodiments, the input conduit 120 is secured to an output of the primary vessel 110 by a cast seal formed between the input conduit 120 and a cap (not shown) secured about the opening 112 of the primary vessel 110. The input conduit 120 includes a second terminus or end 128 that is secured to the input cap 15 (FIG. 2) of the hub assembly 10 about the inlet 51. The second end 128 of the input conduit 120 may be secured to the input cap 15 by a cast seal formed between the second end 128 and the body 50 of the input cap 15. The input conduit 120 may be secured to the input cap 15 before the hub assembly 10 is assembled. For additional detail on a suitable cast seals, reference may be made to U.S. Pat. No. 9,376,305 ("the '305 Patent"), the entire contents of which are hereby incorporated reference.

The input conduit 120 may include a deformable sleeve 126 at a location that facilitates substantially sealing, cutting, and detaching the deformable sleeve 126. The deformable sleeve 126 is formed of a material having plasticity such that pressure applied to the sleeve causes the deformable sleeve 126 to deform about and seal the input conduit 120 and upon continued application of pressure to the deformable sleeve 126, the deformable sleeve 126 and input conduit 120 are cut and the deformable sleeve 126 retains a deformed shape, thereby substantially sealing the input conduit 120. For additional detail on a suitable deformable sleeve, reference may be made to U.S. Pat. No. 8,505,586, the entire contents of which are hereby incorporated by reference.

The input conduit 120 is a flexible conduit and may be formed of thermoplastic tubing, elastomeric tubing, or a combination of thermoplastic and elastomeric tubing. The input conduit 120 may pass through a pump 170 positioned between the primary vessel 110 and the hub assembly 10. The pump 170 may be a peristaltic pump having a pump head 174 that rotates to advance a fluid through the input conduit 120. The pump 170 may include a deformable collar 176 dispose substantially about the input conduit 120 to allow for allow the pump head 174 to compress the input conduit 120 without directly contacting the input conduit 120. The pump 170 is configured to regulate a pressure of the fluid delivered by the input conduit 120 to the hub assembly 10. The pump 170 may increase a pressure or decrease a pressure of fluid within the input conduit 120 to deliver a desired pressure of fluid to the hub assembly 10.

Continuing to refer to FIGS. 4-6, the frame assembly 200 is configured to support the hub assembly 10 and position each of the secondary vessels 130 relative to the hub assembly 10. Specifically, the frame assembly 200 is configured to position each of the secondary vessels 130 such that an arc 192 (FIG. 6) of the distribution conduits 160 is tuned to simultaneously provide a precise flow rate of fluid to each of the secondary vessels 130. For example, the fluid distribution system 1 described herein has been shown to distribute fluid from the primary vessel 110 to each of the secondary vessels 130 with a variance of less than ±1% between each of the secondary vessels 130. Thus, the fluid distribution system 1 may allow for improved accuracy and a reduction in time by simultaneously, accurately distributing a fluid from a primary vessel 110 to a plurality of secondary vessels 130. Each of the secondary vessels 130 may be a rigid vessel, e.g., a bottle, or flexible vessel, e.g., a collapsible bag The frame assembly 200 includes a support collar 210, lower arms 220, upper arms 230, and a vessel collar 240. The support collar 210 forms a ring having an outer diameter similar to the diameter of the hub assembly 10. The support collar 210 defines a central receiver 212 with an inner diameter of the ring having a diameter similar to an outer diameter of the alignment nubs 58 (FIG. 2) of the input cap 15. Interaction between the support collar 210 and the alignment nubs 58 may axially align the hub assembly 10 to within the central receiver 212 of the support collar 210. In some embodiments, the support collar 210 defines alignment detents 218 that are sized and dimensioned to receive the alignment nubs 58 of the input cap 15 to axially and rotationally align the hub assembly 10 with the support collar 210. The second end 128 of the input conduit 120 may pass through the central receiver 212 to connect to the inlet 51. In addition, the support collar 210 is supported above the surface supporting the secondary vessels 130 to allow the input conduit 120 to enter from an underside of the hub assembly 10 with a gentle curvature to avoid kinking or restrictions to flow through the input conduit 120. The support collar 210 may be supported about the surface by the secondary vessels 130 or by the lower arms 220 contacting the surface. When the lower arms 220 contact the surface, the secondary vessels 130 may be suspended above the surface by the frame assembly 200. In some embodiments, the entire frame assembly 200 and the second vessels 130 are suspended by a hanger or grip 250 of the frame assembly 200.

As shown, the frame assembly 200 includes five sets of upper and lower arms 220, 230. In some embodiments, the frame assembly 200 includes less than five sets of upper and lower arms 220, 230 or more than five sets of upper and lower arms 220, 230. For example, the frame assembly 200 may include three, four, or six sets of upper and lower arms 220 and 230. In certain embodiments, the number of sets of upper and lower arms 220, 230 is half the number of secondary vessels 130. Such an arraignment may allow for precise a location of each of the secondary vessels 130 while minimizing material of the frame assembly 200 and maximizing access to the secondary vessels 130 and the hub assembly 10.

The lower arms 220 extend from the support collar 210 to a joint 228 where each of the lower arms 220 forms a joint 228 with one of the upper arms 230. The lower arms 220 are substantially S-shaped with a downward arcuate segment 222 adjacent the support collar 210 and an upward arcuate segment 224 adjacent the joint 228. The downward arcuate segment 222 of each lower arm 220 may contact an underlying surface to support or elevate the support collar 210 above the underlying surface. As shown, each of the lower arms 220 is substantially I-shaped in cross-section to increase rigidity thereof. The shape and cross-sectional shape of the lower arms 220 should not been seen as limiting as the lower arms 220 are configured to accurately position and rigidly secure the vessel collar 240 relative to the support collar 210. In certain embodiments, the lower arms 220 may be linear elements, have any suitable cross-section, and include a foot (not shown) that extends downward to contact the underlying surface.

The upper arms 230 extend from the joints 228 to a central hub 238 disposed along a central axis of the frame assembly 210 extending through a central axis of the support collar 210 and the hub assembly 10 when the hub assembly 10 is axially aligned with the support collar 210. Each of the upper arms 230 is secured to one another at the central hub 238. The central hub 238 may include a hanger or grip 250 extending upward therefrom and positioned about the central axis. Each of the upper arms 230 defines a substantially continuous arc from the joint 228 to the central hub 238. Each upper arm 230 may deflect downward adjacent the central hub 238 such that an upper surface of the grip 250 is substantially planar with an apex of each of the upper arms 230. In some embodiments, the central hub 238 is positioned at an apex of each of the upper arms 230 with the grip extending upward from the central hub 238. The deflection downward of each of the upper arms 230 may reduce an overall size of the frame assembly 210. The upper arms 230 may each have a substantially I-shaped cross-section to increase rigidity thereof. The shape and cross-sectional shape of the upper arms 230 should not been seen as limiting as the upper arms 230 are configured to accurately position and rigidly secure the vessel collar 240 relative to the support collar 210. In certain embodiments, the upper arms 230 may be linear elements and have any suitable cross-section.

The vessel collar 240 is configured to accurately secure each of the secondary vessels 130 relative to the support collar 210. The vessel collar 240 is continuous and includes an outer ring 242, arm nodes 244, and vessel receivers 246. The outer ring 242 is a segmented or broken ring that defines an outer radial dimension of the frame assembly 200 and is axially aligned with the central axis of the frame assembly 200. The vessel collar 240 extends inward from the outer ring 242 at each of the arm nodes 244 and vessel receivers 246 to form segments or breaks in the outer ring 242. The outer ring 242 may define a plane above, below, or equal to a plane defined by the support collar 210. The outer ring 242 may form a tangent with an outer side of a neck 132 of each of the secondary vessels 130.

The arm nodes 244 extend inward from the outer ring 242 adjacent each of the joints 228 and define a joint receiver 245 that receives a respective one of the joints 228 to secure the vessel collar 240 to the arms 220, 230. The joints 228 may include a barb 229 that extends through the joint receiver 245 to releasably couple the joint 228 to the joint receiver 245. In some embodiments, each joint 228 is secured to a joint receiver 245 by adhesive or a fastener.

The vessel receivers 246 extend inward from the outer ring 242 and are configured to accurately position and secure the secondary vessels 130 relative to the support collar 210. Each vessel receiver 246 includes an entry 248 defined as a gap in the outer ring 242 and a hooked portion 249 extending inward from the ends of the entry 248. The hooked portion 249 is sized and shaped to circumscribe a lower portion of a neck 132 of a respective secondary vessel 130. The hooked portion 249 may be shaped to circumscribe greater than half of the neck 132 of the secondary vessel 130 such that the entry 248 is smaller than a diameter of the neck 132 such that the hooked portion 249 grips the neck 132 of the secondary vessel 130. In use, when a secondary vessel 130 is secured within a respective vessel receiver 246, the neck 132 may urge the entry 248 apart as the neck 132 passes through the entry 248 with the entry 248 closing behind the neck 132 as the neck 132 is received within the hooked portion 249. As shown, the neck 132 of the secondary vessels 130 is substantially cylindrical in shape and the hooked portion 249 is arcuate to complement the neck 132. In some embodiments, the neck 132 of the secondary vessels 130 may be rectangular in cross-section or have different cross-section. In such embodiments, the hooked portions 249 may be shaped to complement the neck 132. In particular embodiments, the neck 132 includes key (not shown) and the hooked portion 249 includes a keyway (not shown) to orient the secondary container 130 within the vessel receiver 246.

The secondary vessels 130 may define a recess 133 about the neck 132 configured to receive the hook portion 249 therein to secure the secondary vessel 130 to the vessel collar 240. Each secondary vessel 130 may include a vessel cap 136 configured to aseptically close an opening 134 of the secondary vessel 130. The vessel cap 136 may include one or more apertures 138 therethrough that provide access to an interior of the secondary vessel 130. One or more of the apertures 138 may include a tubular member, a vent, a plug, or another element extending therethrough. For example, the vessel cap 136 may include three apertures 138 defined therethrough. Each aperture 138 may include a port 140 extending above and/or below a planar surface of the vessel cap 136. As shown, a first aperture 138a includes an inflow conduit 142 extending therethrough, a second aperture 138b includes an outflow conduit 144 extending therethrough, and a third aperture 138c includes a vent 146 extending therethrough. Each of the inflow conduit 142, outflow conduit 144, or vent 146 may be secured within the respective aperture 138 by an aseptic cast seal as disclosed in the '305 Patent. In addition, the inflow conduit 142 or the outflow conduit 144 may include a deformable sleeve 148 similar to the deformable sleeve 126 of the input conduit 120. The inflow conduit 142 may include an open end 143 opposite the second vessel 130 configured to receive a coupler as detailed below. The outflow conduit 144 may include a securement device or flow regulator on an end opposite the second vessel 130. For example, the outflow conduit 144 may include a securement device 145 that aseptically seals the end of the secondary vessel 130 until the securement device 145 is connected to complementary connector. The vent 146 provides an aseptic vent for the secondary vessel 130 to allow air to escape the secondary vessel 130 as fluid flows into the interior of the secondary vessel 130 through the inflow conduit 142. The vent 146 may allow gasses, e.g., air, to pass while preventing liquid from passing therethrough.

With particular reference to FIG. 5, distribution system 1 includes a distribution conduit 160 secured to each of the conduit connectors 32 of the distribution cap 12 of the hub assembly 10. Each of the distribution conduits 160 has a first end 162 secured to a respective conduit connector 32 and in communication with the plenum 30 of the hub assembly 10 through one of the outlets 33 that is defined through the respective conduit connecter 32. The first end 162 of each distribution conduit 160 may be secured to the respective conduit connector 32 by an aseptic cast seal as disclosed in the '305 Patent. For example, each conduit connector 32 may be potted with a vulcanizable silicone to form a cast seal when the first end 162 is received over the conduit connector 32. The second end 164 of each distribution conduit 160 includes a coupler 166 configured to couple the second end 164 of the distribution conduit 160 to the open end 143 of a respective inflow conduit 142 as shown in FIG. 6.

Continuing to refer to FIG. 6, when the second end 164 of the distribution conduit 160 is coupled to the open end 143 of a respective inflow conduit 142, the distribution conduit 160 and the inflow conduit 142 form a output tube 190 that has a continuous arc between the outlet 33 of the distribution cap 12 and the secondary vessel 130. The lengths of the distribution conduits 160 and the inflow conduits 142 are tuned such that each output tube 190 has the same length between the outlet 33 and the secondary vessel 130. As a result of each of the output tubes 190 having equal length and the frame assembly 200 secures each of the secondary vessels 130 at an equal distance from the distribution cap 12, an arc 192 formed by each output tube 190 between the outlet 33 and the secondary vessel 130 is substantially equal to one another. The arc 192 is tuned such that an equal amount of fluid, e.g., ±1%, is distributed from the distribution cap 12 to each of the secondary vessels 130 as fluid is delivered to the hub assembly 10 through the inlet 51. The vessel cap 136 of each secondary vessel 130 is oriented in a similar orientation relative to the hub assembly 10 such that a distance between the port 141 receiving the inflow conduit 142 and the outlet 33 in communication with the port 141 is substantially equal for each of the secondary vessel 130. For example, the port 141 receiving the inflow conduit 142 may be oriented towards the hub assembly 10.

The pressure or flow rate of fluid into the hub assembly 10 through the inlet 51 may affect an amount of fluid distributed to each of the secondary vessels 130. In addition, the pressure or flow rate of fluid into the hub assembly 10 combined with the arc 192 may affect the accuracy of the flow to each of the secondary vessels 130. The output tubes 190 are sufficiently stiff to maintain the arcs 192 during a distribution process. In addition, the stiffness of the output tubes 190 can allow a user to pick up the fluid distribution system 1 and transport the fluid distribution system 1 while maintaining the arcs 192. For example, the grip 250 may be used to transport the fluid distribution system 1 with the output tubes 190 maintaining the arcs 192 between the hub assembly 10 and the secondary vessels 130.

The assembly of the fluid distribution system 1 is described below with reference to FIGS. 1-6 above. The assembly of the fluid distribution system 1 may occur in a cleanroom with the entire fluid distribution system 1 being sterilized after being assembled and packaged. Initially, the hub assembly 10 is assembled as detailed above. The hub assembly 10 may be provided in an assembled state and in an aseptic manner. In some embodiments, the hub assembly 10 is provided in a sterilized package and opened in an aseptic environment for assembly of the fluid distribution system 1. The distribution cap 12 or the hub assembly 10 may be selected by a number of conduit connectors 32 of the distribution cap 12.

With the hub assembly 10 provided, the input conduit 120 is secured to the inlet 51 (FIG. 2) of the hub assembly 10. The input cap 15 may be potted about the inlet 51 with a vulcanizable silicone to form an aseptic cast seal with the input conduit 120 to secure the input conduit 120 to the input cap 15 such that an input lumen 124 of the input conduit 120 is in fluid communication with the plenum 30 of the hub assembly 10. The distribution conduits 160 are also secured to the conduit connectors 32 of the distribution cap 12 such that a lumen of each distribution conduit 160 is in fluid communication with the plenum 30 through a respective one of the outlets 33. The distribution cap 12 may be potted about each of the conduit connectors 32 with a vulcanizable silicone to form an aseptic cast seal between each of the distribution conduits 160 and respective conduit connector 32 to secure the distribution conduit 160 to the respective conduit connector 32.

With the conduits 120, 160 secured to the hub assembly 10, the hub assembly 10 is positioned on the frame assembly 200. Specifically, the hub assembly 10 is positioned on the support collar 210 of the frame assembly 200. As the hub assembly 10 is positioned on the support collar 210, the input conduit 120 may pass through the central receiver of the support collar 210. As the hub assembly 10 is positioned on the support collar 210, the plate 80 of the lower clamp 18 rests on the support collar 210 with the alignment nubs 58 of the input cap 15 interacting with the support collar 210 to axially align the hub assembly 10 with the support collar 210 and thus, the frame assembly 200. In particular embodiments, the support collar 210 may define detents similar to the detents 76, 86 of the upper and lower clamps 17, 18 (FIG. 2) that are configured to receive the alignment nubs 58 to radially align the hub assembly 10 with the support collar 210. In some embodiments, the input conduit 160 and/or the distribution conduits 160 are secured to the hub assembly 10 after the hub assembly 10 is positioned on the support collar 210 of the frame assembly 200.

With the hub assembly 10 positioned on the support collar 210, the nodes 244 of the vessel collar 240 are secured to the joints 228 of the lower and upper arms 220, 230. The vessel collar 240 is loaded with the secondary vessels 130. In some embodiments, the vessel collar 240 is loaded with the secondary vessels 130 before being secured to the joints 228 and in other embodiments; the vessel collar 240 is secured to the joints 228 and then loaded with the secondary vessels 130.

The secondary vessels 130 are loaded into the vessel receivers 246 of the vessel collar 240 with the vessel caps 136 secured to the secondary vessels 130. Specifically, the neck 132 of each secondary vessel 130 is inserted or pushed through a respective entry 248 of the vessel collar 140 with recess 143 of the neck 132 receiving the hooked portion 249 of the vessel collar 240 to secure the secondary vessel 130 to the vessel collar 240. As the secondary vessels 130 are secured to the vessel collar 240, each secondary vessel 130 is oriented such that the port 141 receiving the inflow conduit 142 is oriented towards the center of the of the vessel collar 240, e.g., towards the support collar 210.

The secondary vessels 130 may be provided assembled with the vessel caps 136 secured to the secondary vessels 130. In addition, the vessel caps 136 may be provided fully assembled with an inflow conduit 142, an outflow conduit 144, and a vent 146 secured to each vessel cap 136. In some embodiments, the vessel caps 136 may be assembled by securing an inflow conduit 142, an outflow conduit 144, and a vent 146 to each vessel cap 136. For example, the ports 141 of the vessel caps 136 may be potted with a vulcanizable silicone to form an aseptic cast seal between each of the inflow conduits 142, the outflow conduits 144, or the vents 146 a respective port 141 of the vessel cap 136. In certain embodiments, the vessel caps 136 may include additional ports 141 that may receive plugs (not shown) to aseptically close the additional ports 141. In particular embodiments, the vessel caps 136 may include less than three ports 141 with either the outlet conduit 144 and/or the vent 146 omitted.

With the secondary vessels 130 loaded into the vessel collar 240 and the vessel collar 240 secured to the arms 230, 240, the coupler 166 of each distribution conduit 160 is coupled to an open end 143 of a respective inflow conduit 142 to form an output tube 190. When the output tube 190 is formed, each output tube 190 forms the arc 192 between the distribution hub 10 and the respective secondary vessel 130. In some embodiments, the secondary vessels 130 may be loaded into the vessel collar 240 at the point of use. For example, when the secondary vessels 130 are large, it may be beneficial to provide the secondary vessels 130 separate from the rest of the fluid distribution system 1. In such embodiments, the inflow conduit 142 can be terminated with a corresponding aseptic connector (not shown) during shipping and before assembly.

When the output tubes 190 are formed with the hub assembly 10 positioned on the support collar 210 and the vessel collar 240 secured at the joints 248, the frame assembly 200 is assembled.

When the frame assembly 200 is assembled, the entire distribution system 1 can be sealed in a single or double bag package and subjected to gamma irradiation to sterilize the assembly of the hub assembly 10 and the frame assembly 200. When irradiated, the entire assembly of the hub assembly 10 and the frame assembly 200 may be provided preassembled. The assembly of the hub assembly 10 and the frame assembly 200 may be assembled as detailed above in a cleanroom, packaged, irradiated, and then shipped to another facility, e.g., a customer facility, for use.

Figure 7:
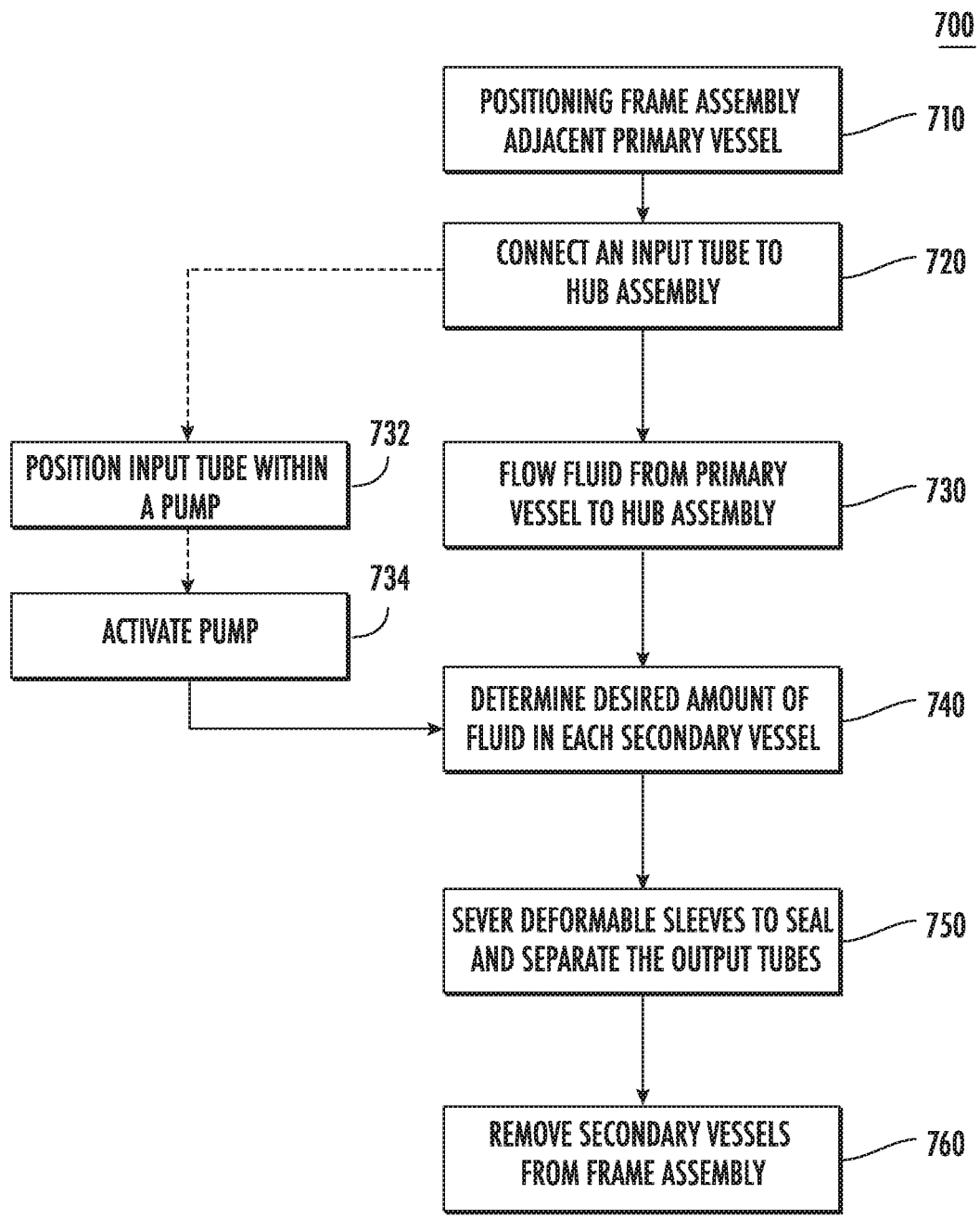
FIG. 7 is a flowchart of an exemplary method of distributing fluid from a primary vessel to a plurality of secondary vessels in accordance with the present disclosure.

With reference to FIG. 7, a method of aseptically distributing a fluid from a first vessel to a plurality of second vessels 700 is described in accordance with the present disclosure with reference to the fluid distribution system 1 of FIGS. 1-6. Initially, a hub assembly 10 and a frame assembly 200 are assembled or provided as detailed above. When the frame assembly 200 is assembled, the hub assembly 10 is positioned on the support collar 210 with the input conduit 120 extending through the support collar 210. In some embodiments, the assembly of the hub assembly 10 and the frame assembly 200 are provided assembled together in a single sterilized package.

With the frame assembly 200 assembled, the frame assembly 200 is positioned adjacent to a primary vessel 110 (Step 710). The primary vessel 110 may be any suitable container for holding a fluid to be distributed to the secondary vessels 130. For example, the primary vessel 110 may be a bag hung from a hanger or may be a rigid container placed on, above, or below a surface supporting the frame assembly 200. The frame assembly 200 may be positioned on a surface in the proximity of the primary vessel 110 or may be hung from a hanger in the proximity of the primary vessel 110. For example, the grip 250 may be utilized to hang the frame assembly 200 in the proximity of the primary vessel 110.

With the frame assembly positioned adjacent the primary vessel 110, the input conduit 120 is connected with the opening 112 of the primary vessel 110 (Step 720). The first end 122 of the input conduit 120 is connected to the opening 112 of the primary vessel 110 with a suitable aseptic connection, e.g., an aseptic connection, a barb connection, a luer connection, a needle connection, etc. The input conduit 120 may also be positioned within a pump 170 between the primary vessel 110 and the hub assembly 10 (Step 732). When the input conduit 120 passes through the pump 170, the pump 170 is used to establish a desired pressure or flow rate of a fluid into the plenum 30 of the hub assembly 10. The pump 170 may increase or decrease a pressure of a fluid from the primary vessel 110.

With the input conduit 120 connected to the primary vessel 110, fluid from within the primary vessel 110 flows through the input conduit 120 into the plenum 30 (FIG. 2) of the hub assembly 10 (Step 730). Fluid may be drawn from the primary vessel 110 by the pump 170. Specifically, the pump 170 may be a peristaltic pump including a rotatable head 174 that is configured to compress the input conduit 120 as the head 174 rotates within the pump 170 to flow the fluid into the plenum 30 through the inlet 51 (Step 734). In some embodiments, the fluid distribution system 1 may flow fluid without a pump. For example, the primary vessel 110 may be pressurized to flow fluid from the primary vessel 110 ion the plenum 30. Alternatively, fluid may flow from the primary vessel 110 into the plenum 30 as a result of gravity only.

As the fluid flows into the plenum 30, pressure within the plenum 30 is increased until the fluid flows from the plenum 30 into the distribution conduits 160 through the outlets 33. The arc 192 of the output tubes 190, including the distribution conduits 160, controls the fluid flow from the plenum 30 into the output tubes 190 such that the fluid flow into each output tube 190 is equal to the fluid flow in each of the other output tubes 190. The output tubes 190 are sufficiently rigid to maintain the arcs 192 during fluid flow. As the fluid flow reaches an apex 194 of the arcs 192, the fluid flows into the secondary vessels 130 through the ports 141. In some embodiments, each vent 146 vents the respective secondary vessel 130 at a predetermined pressure that is greater than a pressure about the distribution system 1, e.g., atmospheric pressure. By venting each of the secondary vessels 130 at the same predetermined pressure, fluid flow into the secondary vessels 130 may be equalized as fluid flow between the secondary vessels 130 may be limited by a pressure within the secondary vessels 130. During distribution of the fluid, the frame assembly 200 may be maintained level such that planes perpendicular to a central longitudinal axis of the hub assembly 10 is are parallel with a ground plane.

When a desired amount of fluid is disposed within each of the secondary vessels 130, the pump 170 may be stopped to terminate fluid flow into the plenum 30 (Step 740). Even with the pump 170 stopped, the pump 170 may maintain a pressure within the plenum 30. In embodiments, without a pump, the fluid flow may be terminated by closing a valve adjacent the primary vessel 110. In some embodiments, the input conduit 120 includes a deformable sleeve 126. In such embodiments, the input conduit 120 may be severed in the deformable sleeve 126 with the deformable sleeve sealing the input conduit 120 as the input conduit 120 is severed. The deformable sleeve 126 may be severed while maintaining an aseptic seal.

With the fluid flow terminated, the deformable sleeve 148 of each inflow conduit 142 of each output tube 190 is severed with the deformable sleeve 148 sealing the input conduit 120 (Step 750). The deformable sleeve 148 forms an aseptic seal on both sides such that the hub assembly 10 and the secondary vessel 130 are each sealed by the deformable sleeve 148. With the secondary vessel 130 sealed by the deformable sleeve 148, the secondary vessel 130 may be removed from the vessel collar 240 (Step 760).

With the secondary vessel 130 removed from the vessel collar 240, the secondary vessel 130 may be used to aseptically transport the fluid therein. The fluid may be removed from the secondary vessel 130 through the outflow conduit 144. In some embodiments, the vent 146 and/or the inflow conduit 142 may be removed from the secondary vessel 130 and the respective ports 141 may be sealed with a plug (not shown).

The method of distributing the fluid detailed above may be utilized to simultaneously distribute an equal amount of fluid from a single vessel into a plurality of secondary vessels. The method and distribution system detailed herein allow for a precise amount of fluid to be distributed into each of the secondary vessels without requiring secondary measurement or flow control valves. The method and distribution system may allow for distribution of fluid in a reduced time, less opportunity for contamination, and less waste when compared to previous methods and distribution systems that may reduce the cost of manufacturing fluids that require distribution from a one vessel to smaller vessels for distribution.

In addition, the method of distributing the fluid detailed above may be reversed to combine fluids from a plurality of small vessels, e.g., secondary vessels 130, into a single large vessel, e.g., primary vessel 110, with a substantially equal amount of fluid being drawn from each of the smaller vessels. In such a method, a pump, e.g., pump 170, may draw fluid from the plenum 30 through the input tube 120 such that fluid is drawn from the smaller vessels through the output tubes 190. As an alternative to the pump 170, the large vessel may be a negative pressure vessel to draw fluid from the smaller vessels. The arcs 192 of the output tubes 190 may be tuned such that a substantially equal amount of fluid is drawn from each of the smaller vessels.

The fluid distribution systems detailed herein may be suitable for use in conveying liquids, mixtures, or suspensions during the manufacture of biopharmaceutical and pharmaceutical products in an aseptic manner. The fluid distribution systems detailed herein are intended to provide aseptic fluid distribution. The fluid distribution systems detailed herein are not particularly limited to use in pharmaceutical development or manufacturing.

The conduits detailed herein, e.g., input conduit 120, inflow conduits 142, outflow conduits 144, or distribution conduits 160, may be flexible conduits suitable for use in medical or pharmaceutical environments. The conduits may be constructed of a thermoset or a thermoplastic polymer. If a thermoset is used, silicones, polyurethanes, fluoroelastomers or perfluoropolyethers may be used for the conduits. If a thermoplastic is used, C-Flex® tubing, block copolymers of styrene-ethylene-butylene-styrene, PureWeld, PVC, polyolefins, polyethylene, blends of EPDM and polypropylene (such as Santoprene™) may be used as construction materials. Semi-rigid thermoplastics including, but not limited to, fluoropolymers PFA, FEP, PTFR, THV, PVDF and other thermoplastics, such as polyamide, polyether sulfone, polyolefins, polystyrene, PEEK, also can be used in one or more portions or sections of the conduits to render them flexible. The conduits may have various inner and outer diameters depending on the intended use of the fluid distribution system 1.

The vessels detailed herein may include, but are not limited to, containers, beakers, bottles, canisters, flasks, bags, receptacles, tanks, vats, vials, conduits, syringes, carboys, tanks, pipes and the like that are generally used to contain liquids, slurries, and other similar substances. The vessels may be closed by a MYCAP™, available from Sartorius Stedim North America. The conduits may terminate in components or vessels that include other aseptic connectors or fittings such as an AseptiQuik® connector available from Colder Products Company of St. Paul Minn., an OPTA aseptic connector available from Sartorius Stedim North America, a ReadyMate connector available from GE Healthcare of Chicago Ill., or other terminus such as syringes, centrifuge conduits, or a plug.

Components of the hub assembly 10 and the frame assembly 200 may include thermoplastics such as polyolefins, polypropylene, polyethylene, polysulfone, polyester, polycarbonate, and glass filled thermoplastics. The hub assembly 10 and the frame assembly 200 may also be made from thermosets such as epoxies, pheonolics, silicone, copolymers of silicone and novolacs. Other suitable materials may include polyamide, PEEK, PVDF, polysulfone, cyanate ester, polyurethanes, and urethane methacrylate. Yet metallic materials, such as stainless steel, aluminum, titanium, etc., or ceramics, such as aluminum oxide, may be used. The present disclosure however is not limited to a junction made from any particular material(s) and any suitable materials or combinations thereof may be used without departing from the scope of the present disclosure.

Additive manufacturing techniques may allow for the creation of structures that may not be capable of being manufactured with traditional molding or machining steps. These structures can lead to a reduction in packaging space and a reduction in components, which can help to reduce leak points and reduce the costs of assembling the fluid distribution system 1. For example, the distribution cap 12 or the input cap 15 may be manufactured using additive manufacturing techniques, e.g., three-dimensional printing.

In some embodiments, components of the fluid distribution system 1 may be surface treated to affect appearance, hydrophobicity, and/or surface roughness. In bioprocesses particularly, minimizing surface roughness may minimize the potential for trapped bacteria. Examples of surface treatment can include metalizing with electroless nickel, copper, or other metal to fill in surface pits. A metalized surface may also improve adhesion and allow for inductive heating. In another example, components of the fluid distribution system 1 can be coated with an inorganic material, such as oxides of silicon (glass or glass like) or coated with organometallic materials. Silane coupling agents can be applied to the surface to change the surface hydrophobicity. If metallic, components of the fluid distribution system 1 can be electropolished to improve surface roughness. The components of the fluid distribution system 1 further can be polished using paste abrasives, such as paste abrasives available from Extrude Hone LLC of Irwin, Pa.

The cast seals detailed herein may be constructed from a self-leveling, pourable silicone such as room-temperature-vulcanizing ("RTV") silicone. The RTV silicone may be a two-component system (base plus curative) ranging in hardness from relatively soft to a medium hardness, such as from approximately 9 Shore A to approximately 56 Shore A. Suitable RTV silicones include Wacker® Elastocil® RT 622, a pourable, addition-cured two-component silicone rubber that vulcanizes at room temperature (available from Wacker Chemie AG), and Rhodorsil® RTV 1556, a two-component, high strength, addition-cured, room temperature or heat vulcanized silicone rubber compound (available from Blue Star Silicones). Both the Wacker® Elastocil® RT 622 and the Bluestar Silicones Rhodorsil® RTV 1556 have a viscosity of approximately 12,000 cP (mPa·s). The aforementioned silicones and their equivalents offer low viscosity, high tear cut resistance, high temperature and chemical resistance, excellent flexibility, low shrinkage, and the ability to cure a cast silicone seal at temperatures as low as approximately 24° C. (approximately 75° F.). The cast seal may also be constructed from dimethyl silicone or low temperature diphenyl silicone or methyl phenyl silicone. An example of phenyl silicone is Nusil MED 6010. Phenyl silicones are particularly appropriate for cryogenic applications. In some embodiments, the casting agent is a perfluoropolyether liquid. The perfluoropolyether liquid may be Sifel 2167, available from Shin-Etsu Chemical Co., Ltd. of Tokyo, Japan. In some instances, a primer may be used to promote bonding of the cast seal to the components of the fluid distribution system 1. Suitable primers are SS-4155 available from Momentive™, Med-162 available from NuSil Technology, and Rodorsil® V-O6C available from Bluestar Silicones of Lyon, France.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A fluid distribution system configured to distribute fluid from a primary vessel to a plurality of secondary vessels, the fluid distribution system comprising:
   a hub assembly comprising:
      an input cap including a body having an inlet defined therethrough, the inlet defined about a central axis of the hub assembly, the inlet configured to receive an input tube thereabout; and
      a distribution cap sealingly secured to the input cap with a plenum being defined between the input and distribution caps, the distribution cap including a plurality of conduit connectors extending from a surface of the distribution cap, each conduit connector of the plurality of conduit connectors including an outlet defined therethrough and in fluid communication with the inlet via the plenum, the plurality of conduit connectors disposed in a ring about the central axis of the hub assembly;
   a plurality of output tubes, each output tube extending from a respective conduit connector to a respective secondary vessel; and
   a frame assembly supporting the hub assembly with the central axis of the hub assembly coaxially aligned with a central axis of the frame assembly, the frame assembly configured to secure each secondary vessel of the plurality of secondary vessels a predetermined distance relative to the hub assembly such that each output tube forms an arc between the respective conduit connector and the respective secondary vessel, the arc tuned to balance a flow rate of fluid from the hub assembly between the output tubes, the frame assembly configured to support the hub assembly and the plurality of secondary vessels such that fluid provided to the inlet is simultaneously distributed to each secondary vessel, the frame assembly supporting the hub assembly with the input cap below the distribution cap.

2. The fluid distribution system according to claim 1, wherein the hub assembly further comprises:
   a first clamp disposed over the distribution cap and engaged with the input cap to secure the input cap to the distribution cap, the plurality of conduit connectors extending through an opening of the first clamp; and
   a second clamp disposed over the input cap and engaged with the distribution cap to secure the distribution cap to the input cap, the body of the input cap extending through an opening of the second clamp.

3. The fluid distribution system according to claim 1, further comprising a plurality of distribution conduits, each distribution conduit of the plurality of distribution conduits including a first end seemingly secured to a respective conduit connector of the plurality of conduit connectors of the distribution cap with a distribution lumen of the distribution conduit in fluid communication with the plenum through the outlet of the respective conduit connector.

4. The fluid distribution system according to claim 3, wherein each distribution conduit of the plurality of distribution conduits includes a coupler secured within a second end opposite the first end, the coupler configured to be received within an inlet conduit of a respective secondary vessel of the plurality of secondary vessels.

5. The fluid distribution system according to claim 3, further comprising a plurality of secondary vessels, each of the secondary vessels including an inlet conduit in fluid communication with the plenum through a respective distribution conduit of the plurality of distribution conduits.

6. The fluid distribution system according to 5, wherein each inlet conduit and respective distribution conduit forms the output tube between the respective conduit connector and a respective secondary vessel.

7. The fluid distribution system according to claim 5, wherein each of the secondary vessels is a bottle or a bag.

8. The fluid distribution system according to claim 1, further comprising an input tube having a first end seemingly secured to the input cap and defining an input lumen in fluid communication with the plenum through the inlet, the input tube having a second end configured to be secured to the primary vessel.

9. The fluid distribution system according to claim 8, further comprising a pump disposed about the input tube, the pump configured to pump fluid from the primary vessel and into the plenum of the hub assembly through the input tube.

10. The fluid distribution system according to claim 1, wherein the frame assembly includes a support collar, lower arms, and a vessel collar, the support collar supporting and coaxially aligning the hub assembly with the central axis of the frame assembly, the support collar defining the central axis of the frame assembly.

11. The fluid distribution systems according to claim 10, wherein each of the lower arms extends between the support collar and a joint, the vessel collar secured at each joint.

12. The fluid distribution system according to claim 11, wherein the vessel collar releasably secured at each joint.

13. The fluid distribution system according to claim 11, wherein the vessel collar includes an outer ring, arm nodes, and vessel receivers, each arm node extending inward from the outer ring and configured to secure to a joint of a respective lower arm, each vessel receiver extending inward from the outer ring, defining an entry at the outer ring, and configured to secure one of the secondary vessels to the vessel collar.

14. The fluid distribution system according to claim 11, wherein the frame assembly includes upper arms and a central hub, each upper arm extending from a respective joint to the central hub, the central hub disposed about the central axis and offset from the support collar along the central axis.

15. A fluid distribution system comprising:
 an input tube;
 a plurality of vessels, each vessel including an inflow conduit and an outflow conduit;
 a distribution hub comprising:
  an input end including a single inlet defined therethrough, the input tube secured about the input end and in fluid communication with the inlet;
  a distribution end including a plurality of conduit connectors, each conduit connector in fluid communication with a respective inflow conduit; and
  a plenum disposed within the distribution hub between the inlet tube and the inflow conduits and configured to provide fluid communication between the inlet tube and the inflow conduits, the plenum having plenum openings configured to simultaneously distribute substantially equal amounts of fluid through each plenum opening to each inflow conduit and to the vessels; and
 a frame assembly supporting the distribution hub with the input end below the distribution end, the frame assembly configured to support the distribution hub and the plurality of vessels such that each inflow conduit forms an arc between the respective conduit connector and the respective vessel, the arc tuned to balance a flow rate of fluid from the hub assembly such that fluid provided to the inlet is simultaneously distribute to each vessel.

16. The fluid distribution system according to claim 15, wherein the frame assembly supports each of the vessels in substantially the same plane relative to one another.

17. The fluid distribution system according to claim 15, wherein the frame assembly positions each vessel a substantially equal distance from the hub such that the inflow conduits of the respective vessels form an arc segment between the hub and the vessel.

18. The fluid distribution system according to claim 15, wherein the inflow conduits are substantially the same length and have substantially the same inner diameter.

19. The fluid distribution system according to claim 15, wherein each of the inflow conduits includes a deformable sleeve configured to aseptically seal the inflow conduit when the deformable sleeve is cut.

20. The fluid distribution system according to claim 15, wherein each vessel of the plurality of vessels is selected from the group consisting of a bottle, a flask, a bag, a vial, a syringe, and a receptacle.

\* \* \* \* \*